(12) United States Patent
Moy et al.

(10) Patent No.: US 9,241,928 B2
(45) Date of Patent: Jan. 26, 2016

(54) ANTIMICROBIAL COMPOUNDS

(75) Inventors: Terence Moy, Wayland, MA (US); Annie Conery, Belmont, MA (US); Kim Lewis, Newton, MA (US); Frederick M. Ausubel, Newton, MA (US); Read Pukkila-Worley, Cambridge, MA (US)

(73) Assignees: The General Hospital Corporation, Boston, MA (US); Northeastern University, Boston, MA (US)

( * ) Notice: Subject to any disclaimer, the term of this patent is extended or adjusted under 35 U.S.C. 154(b) by 839 days.

(21) Appl. No.: 13/379,575

(22) PCT Filed: Jun. 25, 2010

(86) PCT No.: PCT/US2010/040018
§ 371 (c)(1),
(2), (4) Date: May 9, 2012

(87) PCT Pub. No.: WO2010/151784
PCT Pub. Date: Dec. 29, 2010

(65) Prior Publication Data
US 2012/0232110 A1    Sep. 13, 2012

Related U.S. Application Data

(60) Provisional application No. 61/220,842, filed on Jun. 26, 2009.

(51) Int. Cl.
| | | |
|---|---|---|
| *A61K 31/44* | (2006.01) | |
| *A61K 31/427* | (2006.01) | |
| *A61K 31/4427* | (2006.01) | |
| *A61K 31/4725* | (2006.01) | |
| *A61K 31/501* | (2006.01) | |

(52) U.S. Cl.
CPC ............... *A61K 31/427* (2013.01); *A61K 31/44* (2013.01); *A61K 31/4427* (2013.01); *A61K 31/4725* (2013.01); *A61K 31/501* (2013.01)

(58) Field of Classification Search
CPC ..................................................... A61K 31/44
USPC ........................................................ 514/183
See application file for complete search history.

(56) References Cited

U.S. PATENT DOCUMENTS

| | | |
|---|---|---|
| 2005/0043369 A1 | 2/2005 | Markham et al. |
| 2006/0217377 A1 | 9/2006 | Gonzalez et al. |
| 2008/0269213 A1 | 10/2008 | Bursavich et al. |

FOREIGN PATENT DOCUMENTS

| | | |
|---|---|---|
| WO | WO 2008-066576 | 6/2008 |
| WO | WO 2009-023343 | 2/2009 |
| WO | WO 2010-151784 | 12/2010 |

OTHER PUBLICATIONS

Emerson et al. ("Some 2-acetylthiophene derivatives and related acetophenone analogs" J. Org. Chem., 1948, 13, 722-728).*
Moy et al., "High-Throughput Screen for Novel Antimicrobials using a Whole Animal Infection Model," ACS Chemical Biology, Author Manuscript, Jul. 17, 2010.
Moy et al., "High-Throughput Screen for Novel Antimicrobials using a Whole Animal Infection Model," ACS Chemical Biology, 4(7):527-533 (2009).
International Search Report and Written Opinion dated Mar. 31, 2011 issued in international application No. PCT/US2010/040018, 12 pgs.
Gross et al., "Discovery of O-GlcNAc Transferase Inhibitors," J. Am. Chem. Soc. 127(42):14588-14589 (2005) and its supporting documents.
Junker et al., "High-Throughput Screens for Small-Molecule Inhibitors of *Pseudomonas aeruginosa* Biofilm Development," Antimicrobial Agents and Chemotherapy 51(10): 3582-3590 (2007).

* cited by examiner

*Primary Examiner* — Yong Chong
(74) *Attorney, Agent, or Firm* — Fish & Richardson P.C.

(57) ABSTRACT

This disclosure relates to compositions including certain compounds identified by a quantitative, high throughput assay to be effective in inhibiting the ability of a bacterium to kill a host organism, as well as methods for using these compounds for treating bacterial infections.

2 Claims, 9 Drawing Sheets

ANTIMICROBIAL COMPOUNDS

STATEMENT REGARDING FEDERALLY SPONSORED RESEARCH

The invention disclosed herein was made in part with Government funding, and the Government has certain rights in the invention. In particular, portions of the invention disclosed herein were funded, in part, under Grant No. AI072508 awarded by National Institutes of Health (NIH) and under Contract No. N01-CO-12400 awarded by National Cancer Institute's Initiative for Chemical Genetics, NIH.

CROSS REFERENCE TO RELATED APPLICATIONS

This application is a U.S. National Phase Application under 35 U.S.C. §371 of International Patent Application No. PCT/US2010/040018, filed Jun. 25, 2010, which claims priority to U.S. Provisional Application Ser. No. 61/220,842, filed Jun. 26, 2009, the contents of which are hereby incorporated by reference.

BACKGROUND

The growing problem of antibiotic resistant bacteria (see, e.g., Chambers H. F., Emerg. Infect. Dis. 7:178-182 (2001); Hecht D. W., Clin. Infect. Ilis. 39:92-97 (2004); Jacobs M. R., Am. J. Med. 117 Suppl. 3A:3S-15S (2004); Molbak K., Clin. Infect. Dis. 41:1613-1620 (2005); Shah et al., Res. Microbiol. 155:409-421 (2004); Wisplinghoff et al., Clin. Infect. Dis. 39:309-3 17 (2004); and Zinner S. H., Expert Rev. Anti. Infect. Ther. 3:907-913 (2005)) points to a need for new anti-infective therapies. However, the rate of new antimicrobial discovery is unlikely to meet the expected need for the foreseeable future (see Boggs et al., Clin. Microbiol. Infect. 10 Suppl. 4:32-36 (2004); Bush K., Clin. Microbiol. Infect. 10 Suppl. 4:10-17 (2004); Dougherty et al., Curr. Pharm. Des. 8:1119-1135 (2002); Schmid M. B., Nat. Rev. Microbiol. 2:739-746 (2004); Silver L. L., IDrugs 8:651-655 (2005); and Walsh C., Nat. Rev. Microbiol. 1:65-70 (2003)). Specific problems include the over-mining or exhaustion of cultivable microorganisms (see Osburne et al., ASM News 66:411-417 (2000)), a high background of toxic compounds or compounds with poor pharmacokinetic properties in synthetic compound libraries (see Projan et al., Clin. Microbiol. Infect. 10 Suppl. 4:18-22 (2004); and Lipinski et al., Nature 432: 855-861 (2004)), and the inability of most synthetic leads to penetrate across the multi-drug resistance (MDR) barrier of Gram-negative bacteria (see Li et al., Drugs 64:159-204 (2004)). The increased use of in vitro assays for small molecule discovery that bear little resemblance to the biological systems in which the drugs need to function may also be responsible for the decline in the rate of drug discovery (see Lipinski et al., Nature 432:855-861 (2004); Horrobin D. F., Nat. Rev. Drug Discov. 2:151-154 (2003); Williams M., Curr. Opin. Investig. Drugs 5:29-33 (2004)). Thus, there is a need for developing new antimicrobial compounds.

SUMMARY

This disclosure is based on the discovery that certain compounds were identified by a quantitative, high throughput *Caenorhabditis elegans* assay to be effective in treating bacterial infections. In particular, one or more of these compounds identified by this assay unexpectedly exhibited in vivo antimicrobial activity even though they did not exhibit significant in vitro antimicrobial activity.

In one aspect, this disclosure features pharmaceutical compositions that include, e.g., as an active agent, a pharmaceutically acceptable carrier and a compound of formula (I):

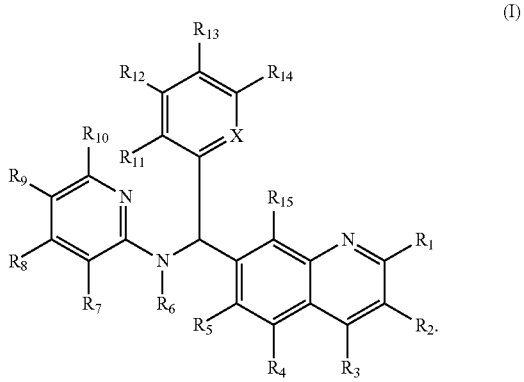

In formula (I), X can be N or $C(R_a)$, in which $R_a$ can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; each of $R_1$, $R_2$, $R_3$, $R_4$, $R_5$, $R_7$, $R_8$, $R_9$, $R_{10}$, $R_{11}$, $R_{12}$, $R_{13}$, $R_{14}$, and $R_{15}$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_b$, $SR_a$, $COOR_b$, $OC(O)R_b$, $C(O)R_b$, $C(O)NR_bR_c$, or $NR_bR_c$, in which each of $R_b$ and $R_c$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and $R_6$ can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (I), a subset of the compounds described above are those in which X is $C(R_a)$. In these compounds, $R_4$ can be halo (e.g., chloro); $R_{11}$ can be H or halo (e.g., fluoro); $R_{12}$ can be H or halo (e.g., fluoro); and $R_{15}$ can be $OR_b$ (e.g., OH). Examples of such compounds include

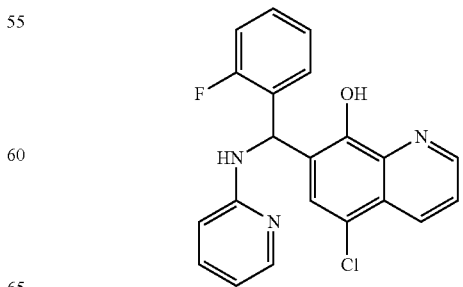

(i.e., Compound 1) and

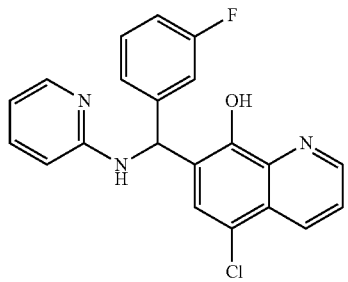 [SMILES: Oc1c(C(Nc2ccccn2)c2cccc(F)c2)cc(Cl)c2cccnc12]

(i.e., Compound 2). Referring to formula (I), another subset of the compounds described above are those in which X is N. In these compounds, $R_4$ can be halo (e.g., chloro) and $R_{15}$ can be $OR_b$ (e.g., OH). An example of such compounds is

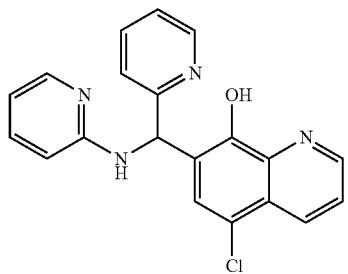 [SMILES: Oc1c(C(Nc2ccccn2)c2ccccn2)cc(Cl)c2cccnc12]

(i.e., Compound 3).

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also included two or more fused rings in which each ring is one of the just-mentioned groups.

In another aspect, this disclosure features pharmaceutical compositions that include, e.g., as an active agent, a pharmaceutically acceptable carrier and a compound of formula (II):

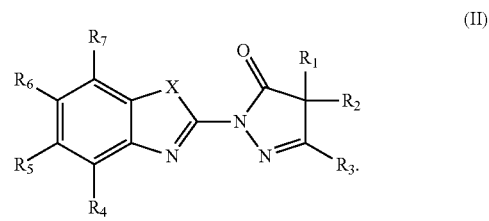

(II)

In formula (II), X can be S or $N(R_a)$, in which $R_a$ can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; each of $R_1$, $R_2$, $R_3$, $R_4$, $R_5$, $R_6$, and $R_7$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_b$, $SR_a$, $COOR_b$, $OC(O)R_b$, $C(O)R_b$, $C(O)NR_bR_c$, or $NR_bR_c$, in which each of $R_b$ and $R_c$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (II), a subset of the compounds described above are those in which X is S. In these compounds, $R_3$ can be $C_1$-$C_{10}$ alkyl (e.g., t-butyl) and $R_6$ can be halo (e.g., chloro). An example of such compounds is

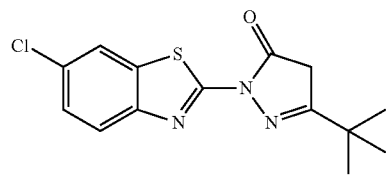 [SMILES: CC(C)(C)C1=NN(c2nc3ccc(Cl)cc3s2)C(=O)C1]

(i.e., Compound 4). Referring to formula (II), another subset of the compounds described above are those in which X is $N(R_a)$. In these compounds, $R_1$ can be $C_1$-$C_{10}$ alkyl optionally substituted with aryl (e.g., methyl substituted with phenyl) and $R_3$ can be $C_1$-$C_{10}$ alkyl (methyl). An example of such compounds is

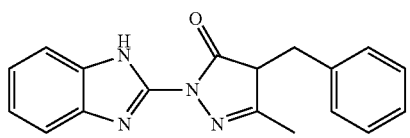 [SMILES: CC1=NN(c2nc3ccccc3[nH]2)C(=O)C1Cc1ccccc1]

(i.e., Compound 5).

In still another aspect, this disclosure features pharmaceutical compositions that include, e.g., as an active agent, a pharmaceutically acceptable carrier and a compound of formula (III):

(III)

In formula (III), each of $R_1$, $R_2$, $R_3$, $R_4$, $R_5$, $R_6$, $R_7$, and $R_8$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, or $NR_aR_b$, in which each of $R_a$ and $R_b$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (III), a subset of the compounds described above are those in which $R_3$ is halo (e.g., chloro) and $R_6$ is $COOR_a$ (e.g., COOH). An example of such compounds is

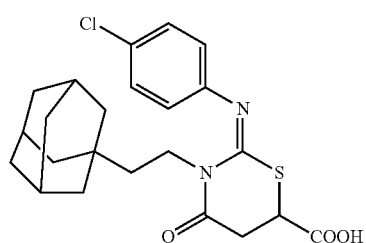 [SMILES: O=C(O)C1CC(=O)N(CCC23CC4CC(CC(C4)C2)C3)/C(=N\c2ccc(Cl)cc2)S1]

(i.e., Compound 6).

In still another aspect, this disclosure features pharmaceutical compositions that include, e.g., as an active agent, a pharmaceutically acceptable carrier and a compound of formula (IV):

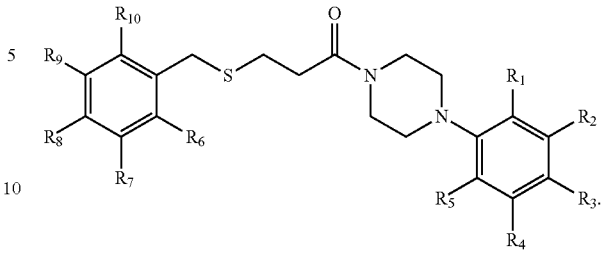

(IV)

In formula (IV), each of $R_1$, $R_2$, $R_3$, $R_4$, $R_5$, $R_6$, $R_7$, $R_8$, $R_9$, and $R_{10}$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, or $NR_aR_b$, in which each of $R_a$ and $R_b$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (IV), a subset of the compounds described above are those in which $R_8$ is halo (e.g., chloro). An example of such compounds is

(i.e., Compound 7).

In still another aspect, this disclosure features pharmaceutical compositions that include, e.g., as an active agent, a pharmaceutically acceptable carrier and a compound of formula (V):

(V)

In formula (V), each of $R_1$, $R_2$, $R_3$, $R_4$, $R_5$, and $R_6$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (V), a subset of the compounds described above are those in which $R_1$ is $SR_a$ (e.g., $SCH_3$). An example of such compounds is

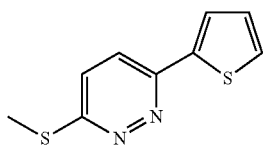

(i.e., Compound 8).

In still another aspect, this disclosure features pharmaceutical compositions that include, e.g., as an active agent, a pharmaceutically acceptable carrier and a compound of formula (VI):

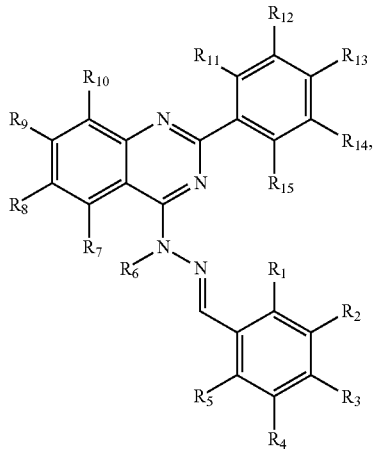

(VI)

In formula (VI), each of $R_1$, $R_2$, $R_3$, $R_4$, $R_5$, $R_7$, $R_8$, $R_9$, $R_{10}$, $R_{11}$, $R_{12}$, $R_{13}$, $R_{14}$, and $R_{15}$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, or $NR_aR_b$, in which each of $R_a$ and $R_b$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and $R_6$ can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (VI), a subset of the compounds described above are those in which $R_1$ is $OR_a$ (e.g., OH); $R_2$ is $C_1$-$C_{10}$ alkyl (e.g., $CH_3$); $R_3$ is $OR_a$ (e.g., OH); $R_6$ is H; and $R_{13}$ is halo (e.g., chloro). An example of such compounds is

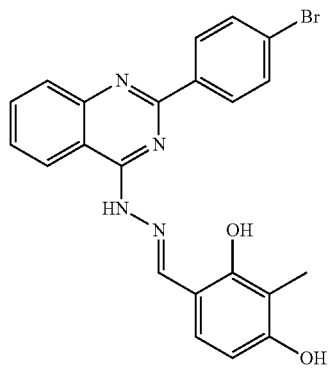 [SMILES: Cc1c(O)ccc(/C=N/Nc2nc(-c3ccc(Br)cc3)nc3ccccc23)c1O]

(i.e., Compound 9).

In still another aspect, this disclosure features pharmaceutical compositions that include, e.g., as an active agent, a pharmaceutically acceptable carrier and a compound of formula (VII):

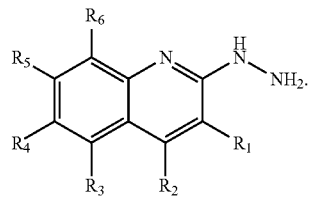

(VII)

In formula (VII), each of $R_1$, $R_2$, $R_3$, $R_4$, $R_5$, and $R_6$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_aOC(O)R_a$, $C(O)R_a$, $C(O)NR_aR_b$, or $NR_aR_b$, in which each of $R_a$ and $R_b$, independently, can be H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or a salt thereof.

Referring to formula (VII), a subset of the compounds described above are those in which $R_3$ is $C_1$-$C_{10}$ alkyl (e.g., methyl) or halo (e.g., chloro); $R_5$ is $C_1$-$C_{10}$ alkyl (e.g., methyl) or halo (e.g., chloro); and $R_6$ is $OR_a$ (OH). Example of such compounds include

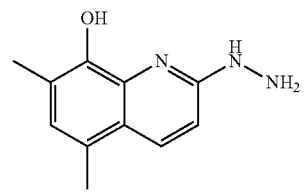

(i.e., Compound 10) and

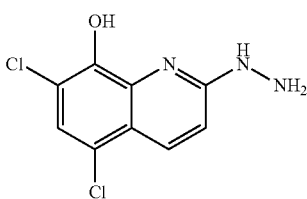 [SMILES: NNc1ccc2c(Cl)cc(Cl)c(O)c2n1]

(i.e., Compound 11).

Other compounds identified by the above-mentioned *Caenorhabditis elegans* assay to be effective in treating bacterial infections include

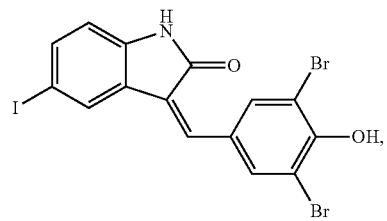

Compound 12

Compound 13
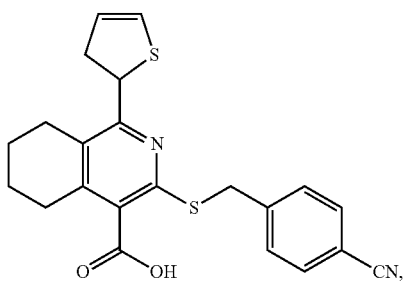
Compound 14
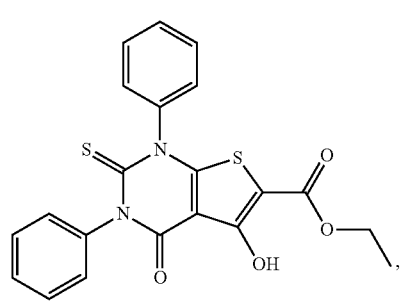
Compound 15
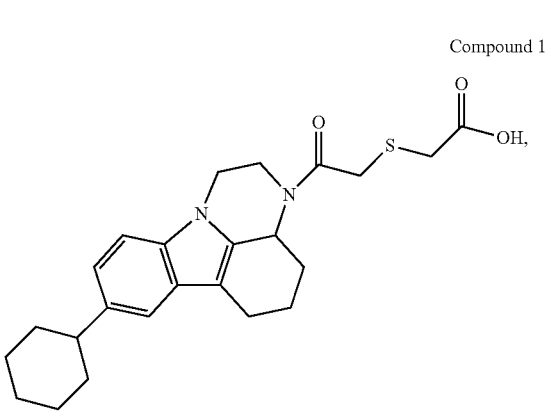
Compound 16
Compound 17
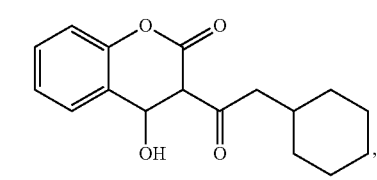
Compound 18
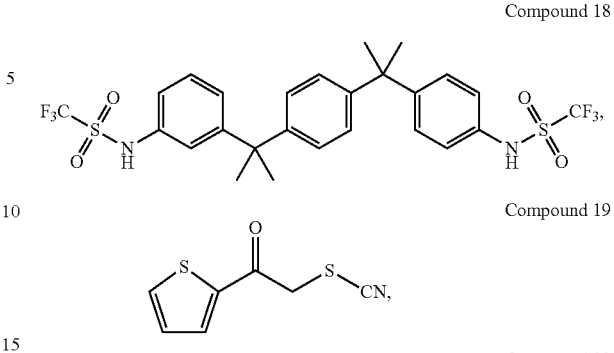
Compound 19
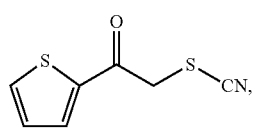
Compound 20
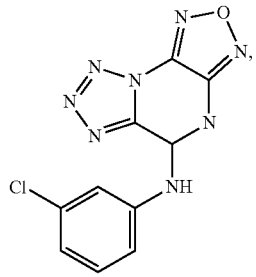
Compound 21
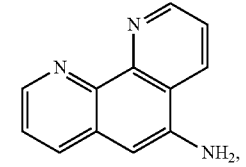
Compound 22
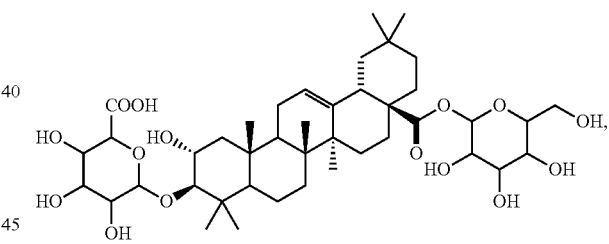
Compound 23
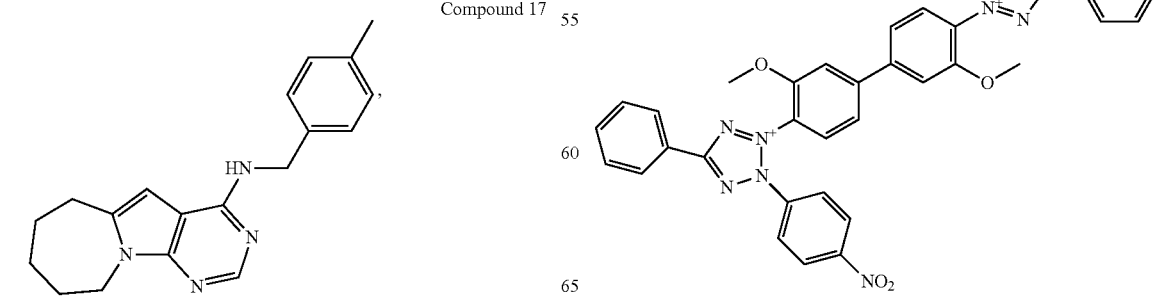

-continued a salt formed between

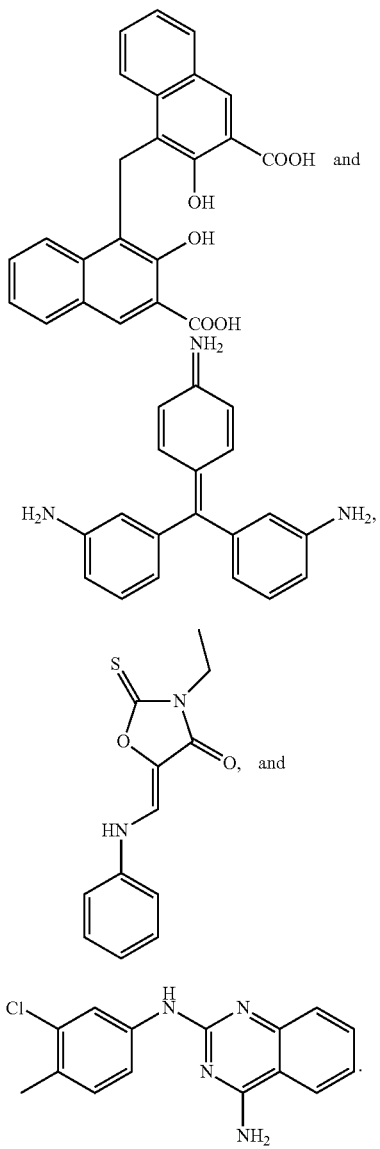

Compound 24

Compound 25

Compound 26

In still another aspect, this disclosure features methods for treating a bacterial infection in a subject (e.g., a host animal such as a human or a plant). The methods include administering to the subject a pharmaceutical composition containing one or more of the above-mentioned compounds in an amount effective to treat the infection. Examples of bacterial infections include community-acquired pneumonia, upper and lower respiratory tract infection, skin and soft tissue infection, bone and joint infection, hospital-acquired infection (e.g., hospital-acquired lung infection), acute bacterial otitis media, bacterial pneumonia, complicated infection, noncomplicated infection, pyelonephritis, intra-abdominal infection, deep-seated abscess, bacterial sepsis, central nervous system infection, bacteremia, wound infection, peritonitis, meningitis, infections after burn, urogenital tract infection, gastrointestinal tract infection, pelvic inflammatory disease, endocarditis, or intravascular infection. For example, the methods can include administering to an immuno-compromised or surgical patient a pharmaceutical composition containing one or more of the above-mentioned compounds in an amount effective to treat a systemic hospital-acquired infection caused by *Enterococcus faecalis* or *Enterococcus faecium*.

The term "treating" or "treatment" refers to administering one or more compounds described above to a subject, who has an above-described bacterial infection, a symptom of such an infection, or a predisposition toward such an infection, with the purpose to confer a therapeutic effect (e.g., to cure, relieve, alter, affect, ameliorate, or prevent) the above-described bacterial infection, the symptom of it, or the predisposition toward it.

The methods of treating bacterial infections described herein can be useful in treating an infection by a Gram-positive bacterium. For example, the method can be used to treat infection by a Gram-positive coccus or by a drug-resistant Gram-positive coccus. The Gram-positive coccus can be selected from *S. aureus, S. epidermidis, S. pneumoniae, S. pyogenes, M catarrhalis, H. influenzae,* and *Enterococcus* spp. Alternatively, the bacterial infection to be treated can be caused by *Chlamydia pneumoniae* or *Chlamydia trachomatis*. The method of treating bacterial infections described above can also be useful in treating an infection is by a Gram-negative bacterium, such as *Pseudonomas aeruginosa, Klebsiella pneumoniae, Escherichia coli, Haemophilus influenzae, Citrobacter fieundii* and *Enterobacter* spp. Further, the method of treating bacterial infections described above can also be useful for treating agriculturally important bacterial infections, such as *Erwinia* spp., *Agrobacterium tumefaciens, Agrobacterium rhizogenes, Pseudomonas syringae,* or *Xanthomonas* spp. infections in plants.

The methods described in this disclosure can also be used to reduce or eliminate the incidence of postoperative infections in a subject undergoing surgical procedures or implantation of prosthetic devices.

This disclosure further features methods of treating an infection by multi-drug resistant bacteria in a subject (e.g., a host animal or plant). The methods include administering to the subject a pharmaceutical composition containing one or more of the above-mentioned compounds in an amount effective to treat the multi-drug resistant infection. Resistant strains of bacteria include penicillin-resistant, methicillin-resistant, quinolone-resistant, macrolide-resistant, and/or vancomycin-resistant bacterial strains. The multi-drug resistant bacterial infections that can be treated by the method described above include, for example, infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

A salt of a compound described above, for example, can be formed between an anion and a positively charged group (e.g., amino) on the compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on the compound. Suitable cations include sodium ion, potassium ion, magnesium ion, calcium ion, and an ammonium cation such as tetramethylammonium ion. The salts of the compounds described above also include those containing quaternary nitrogen atoms.

The compounds described above include the compounds themselves, as well as their prodrugs, and solvates, if applicable. Examples of prodrugs include esters and other pharmaceutically acceptable derivatives, which, upon administration to a subject, are capable of providing active pyrazole compounds. A solvate refers to a complex formed between an active pyrazole compound and a pharmaceutically acceptable solvent. Examples of pharmaceutically acceptable solvents include water, ethanol, isopropanol, ethyl acetate, acetic acid, and ethanolamine.

Also within the scope of this disclosure is a composition containing one or more of the compounds described above for use in treating an above-described bacterial infection, and the use of such a composition for the manufacture of a medicament for the just-mentioned treatment.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
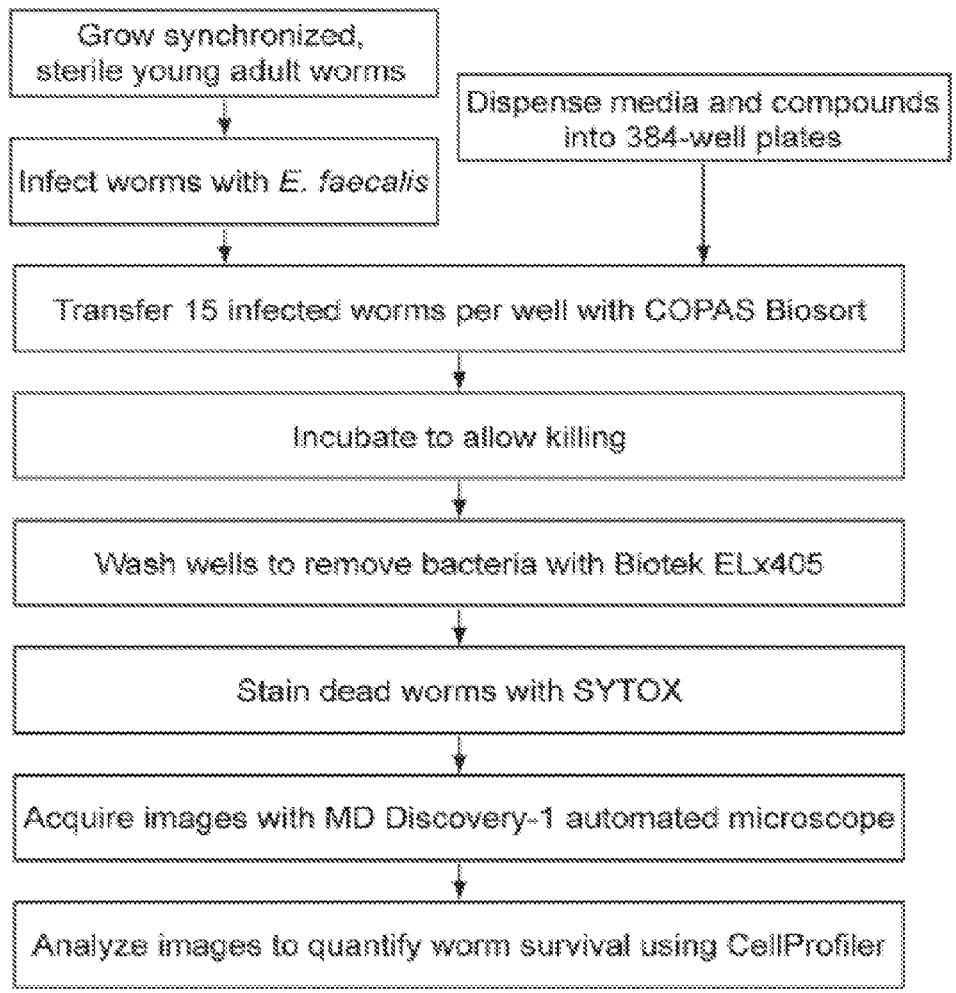
FIG. 1A is a flow chart illustrating the major steps of an automated screening method for determining the efficacy of a candidate compound in inhibiting the ability of *Enterococcus faecalis* to kill *Caenorhabditis elegans*.

This disclosure relates to identifying compounds (e.g., those described in the Summary section above) that inhibit the ability of a bacterium to kill a host organism by using a quantitative, high throughput *Caenorhabditis elegans* assay, as well as using the compounds identified by this assay for treating bacterial infections. In particular, the compounds in the Summary section above (e.g., the compounds of formulae (I)-(VII)) unexpectedly exhibit in vivo antimicrobial activity even though they do not exhibit significant in vitro antimicrobial activity.

All of the compounds described herein can be prepared by methods well known in the art or can be readily obtained from a commercial source. For example, these compounds can be obtained from the following compound libraries or commercial sources: bioactives (e.g., SPBio library from Spectrum/Prestwick (Illkirch, France); and HSCI1 library from Harvard Stem Cell Initiative, Cambridge, Mass.), natural product extracts (Jon Clardy, BCMP, HMS, Boston, Mass.), Analyticon purified natural products (AnalytiCon Discovery GmbH, Potsdam, Germany), Diversity-Oriented Synthesis (Chemical Biology Program, Broad Institute, Cambridge, Mass.), ChemBridge kinases (San Diego, Calif.), ChemDiv (San Diego, Calif.), TimTec (Newark, Del.), MayBridge (Cornwall, UK), and ChemBridge (San Diego, Calif.). A synthesized compound can be purified by a suitable method such as column chromatography, high-pressure liquid chromatography, or recrystallization.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The compounds described above can be identified by a screening method, such as an assay that identifies compounds exhibiting activity in promoting the survival of a host organism (e.g., a nematode *Caenorhabditis elegans*) infected with a human opportunistic pathogen (e.g., *Enterococcus faecalis*). Such a screening method can also be used to identify compounds that increase the lifespan of an organism.

Specifically, the screening method for identifying a candidate compound described herein can include exposing a host organism (e.g., an invertebrate animal or plant host) to a pathogen (e.g., *Enterococcus faecalis*) and incubating the exposed host organism in a liquid medium in the presence of at least one candidate compound. The invertebrate animal or plant host can be contacted with the candidate compound either prior to or after being exposed to the pathogen. A candidate compound that inhibits the ability of the pathogen to kill the host organism can be identified based on the survival or death rate of the host organism. An invertebrate host organism can be, for example, a nematode (e.g., *Caenorhabditis elegans*). Other Examples of the invertebrate host organisms include *Drosophila melanogaster* larvae or adults, *Plutella xylostella* larvae, *Galleria mellonella* larvae, or a plant seedling (e.g., a *Arabidopsis thaliana* seedling). The pathogen that infects the host organism can be, for example, a bacterial pathogen (e.g., *Enterococcus faecalis, Pseudomonas aeruginosa, Pseudomonas syringae, Salmonella typhimurium*, or *Staphylococcus aureus* or *epidermidis*), a fungal pathogen (e.g., *Candida albicans, Candida glabrata, Candida parapsilosis, Crytococcus* spp. (e.g., *C. neoformans, C. gattii, C. grubii*), *Rhodotorula mucilaginosa, Fusarium oxysporum, Botrytis cinerea,* or *Saccharomyces cerevisiae*), a viral pathogen (e.g., vesicular stomatitis virus), a protozoan, a microsporidian pathogen, or a mycobacterium. The exposed host organism can be incubated with at least one candidate compound in a liquid medium. The liquid medium can include, for example, a buffer (e.g., M9 buffer), brain heart infusion media, MS (Murashige and Skoog) medium, cholesterol, and an antibiotic (e.g., kanamycin).

The screening method described above can be carried out in a container that includes an invertebrate animal or a plant host organism that is infected with a pathogen, liquid media, and a candidate compound. The container can be, for example, a 24-well plate, a 48-well plate, a 96-well plate, a 384-well plate, a 1536-well plate, a 3456-well plate, or any other suitable container. In a high throughput screening method, each well of the container may contain a different candidate compound.

The screening method described above can at least in part be automated to obtain a high throughput screening method. For example, a traditional agar-based assay (e.g., an agar based *C. elegans-E. faecalis* infection assay) can be modified so that it could be carried out in a liquid medium in standard microtiter plates. As another example, instead of dispensing infected organisms manually, a large particle sorter can be used to dispense an exact number of infected organisms into each well of a plate (e.g., a 384-well plate).

In addition, because manual screening of the plates is slow, labor intensive and subjective, an automated staining method can be used in a high throughput screening method to distinguish live from dead worms. For example, when a nematode is used as a host organism, the worms can be stained with SYTOX Orange nucleic acid dye. The SYTOX Orange is excluded by living cells in the worms, but readily enters cells with damaged membranes so as to stain dead worms. Because the SYTOX Orange also stains the bacteria in the well, an additional washing step is typically required to remove the bacteria before staining. Further, an automated microscope can be used to acquire an image of the SYTOX fluorescence and a bright field image of each well. The number of worms that survive after incubation can be quantified in an automated manner, e.g., by using an open-source cell image analysis software program CELLPROFILER (Broad Institute, Cambridge, Mass.). A web-based interface for viewing the original images and CELLPROFILER outputs, as well as for performing additional analyses, can also be created.

FIG. 1A illustrates the major steps of an automated high throughput screening method for determining the efficacy of a candidate compound in inhibiting the ability of *Enterococcus faecalis* to kill *Caenorhabditis elegans*.

Figure 1B:
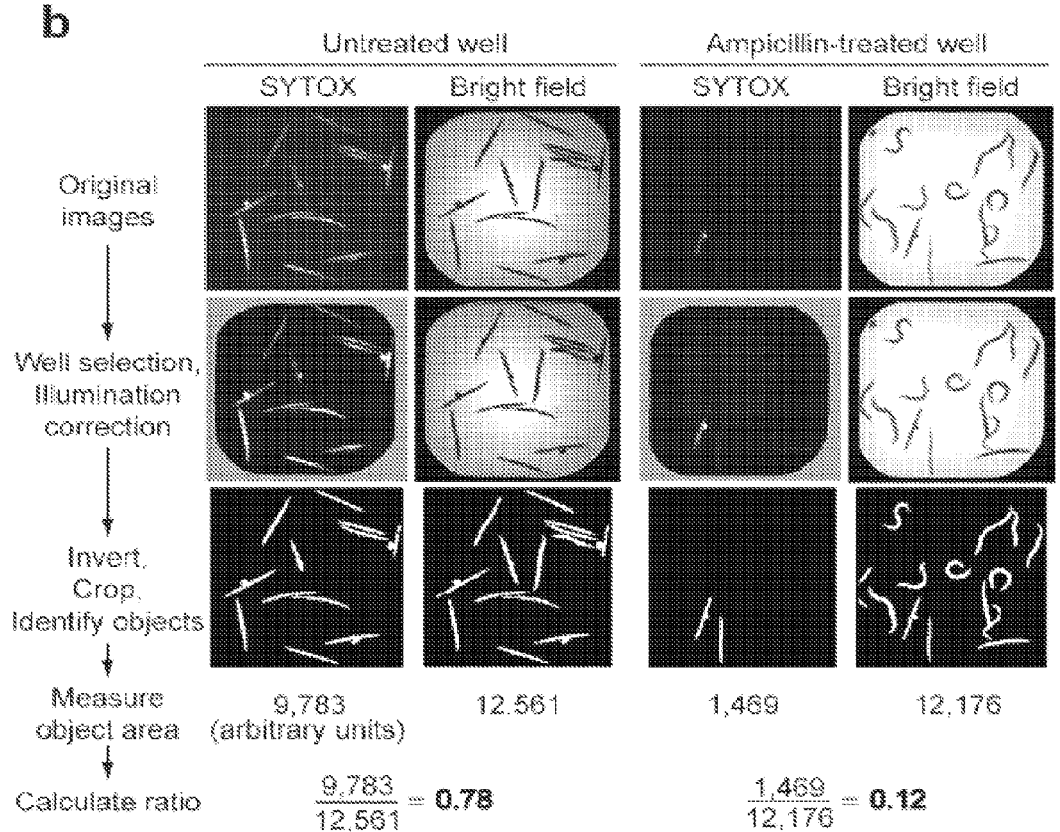
FIG. 1B is a scheme that illustrates using a CELLPROFILER procedure to analyze images obtained from the screening method shown in FIG. 1A.
Figure 2A:
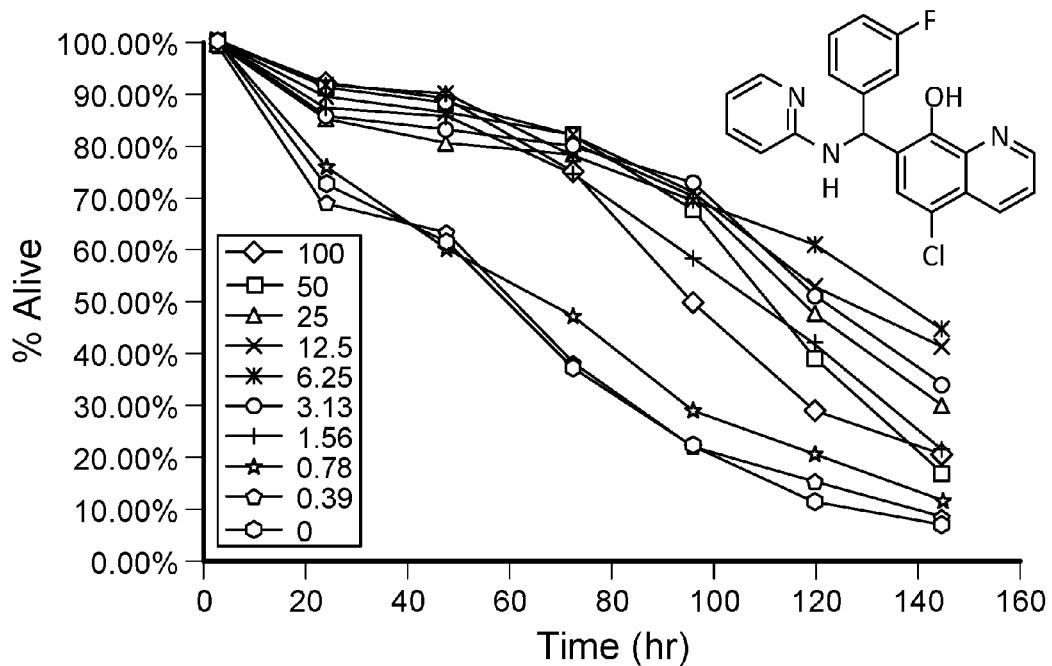
FIGS. 2A-2F include six dose response curves illustrating the kinetics in curing *Enterococcus faecalis* infection in *Caenorhabditis elegans* by using Compounds 2, 4, 6, and 7-9 described in the Summary section above.
Figure 2B:
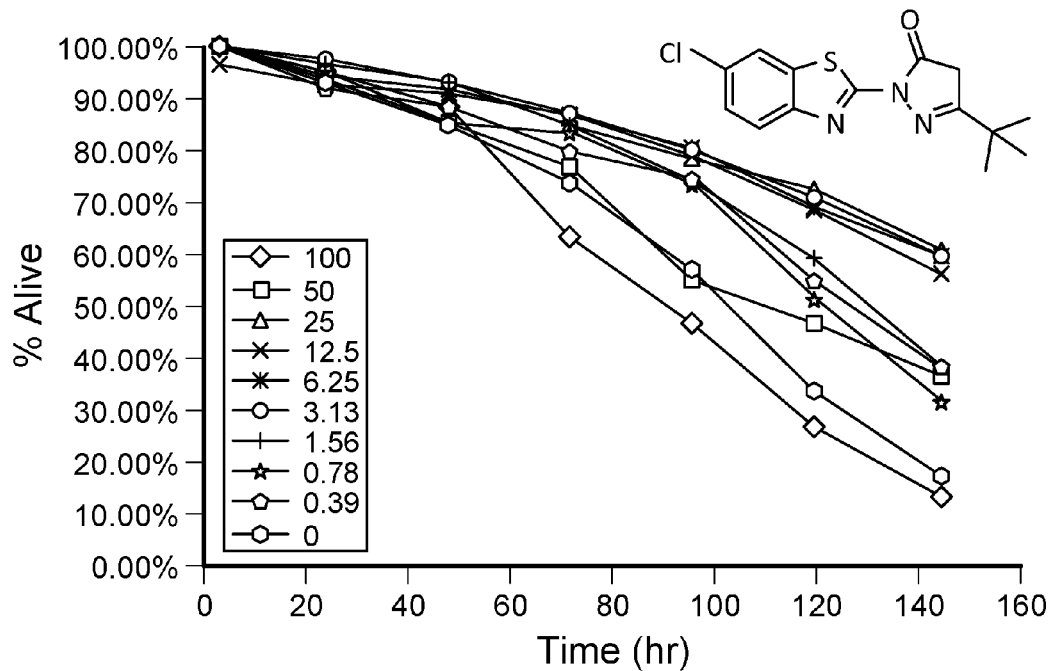
Figure 2C:
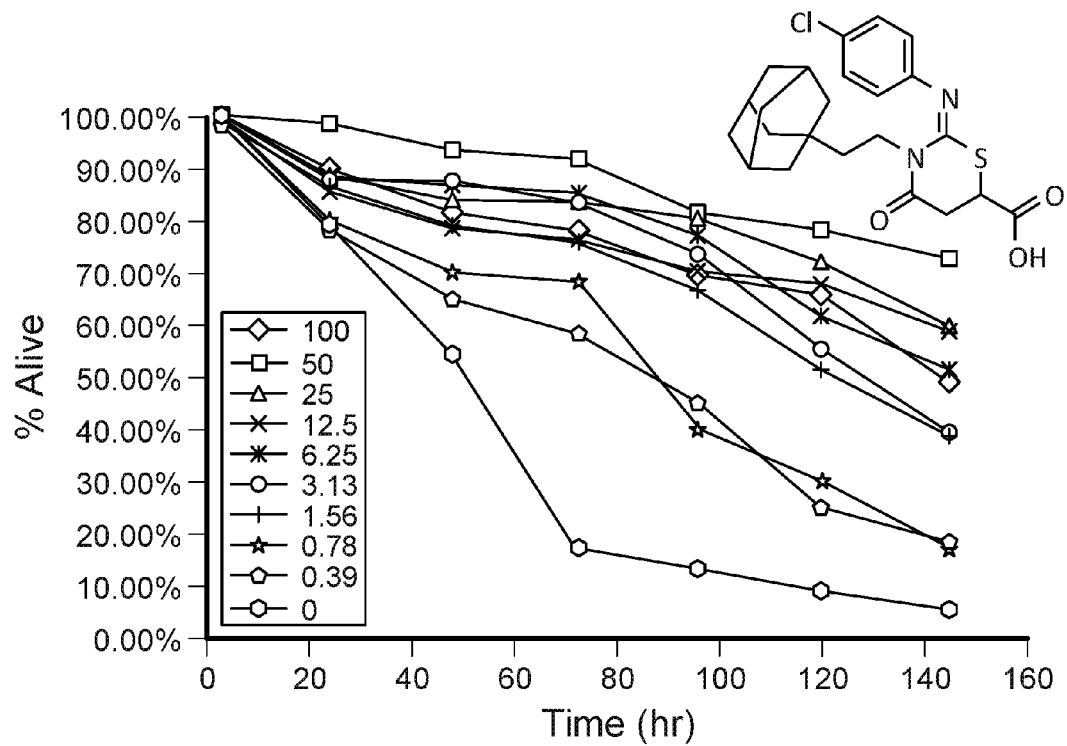
Figure 2D:
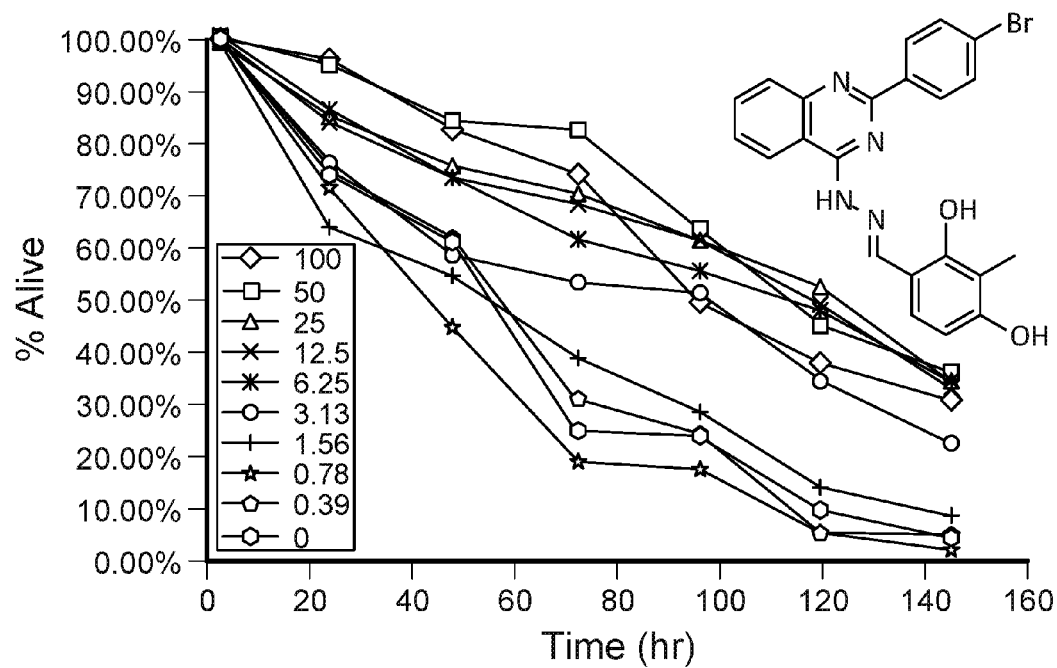
Figure 2E:
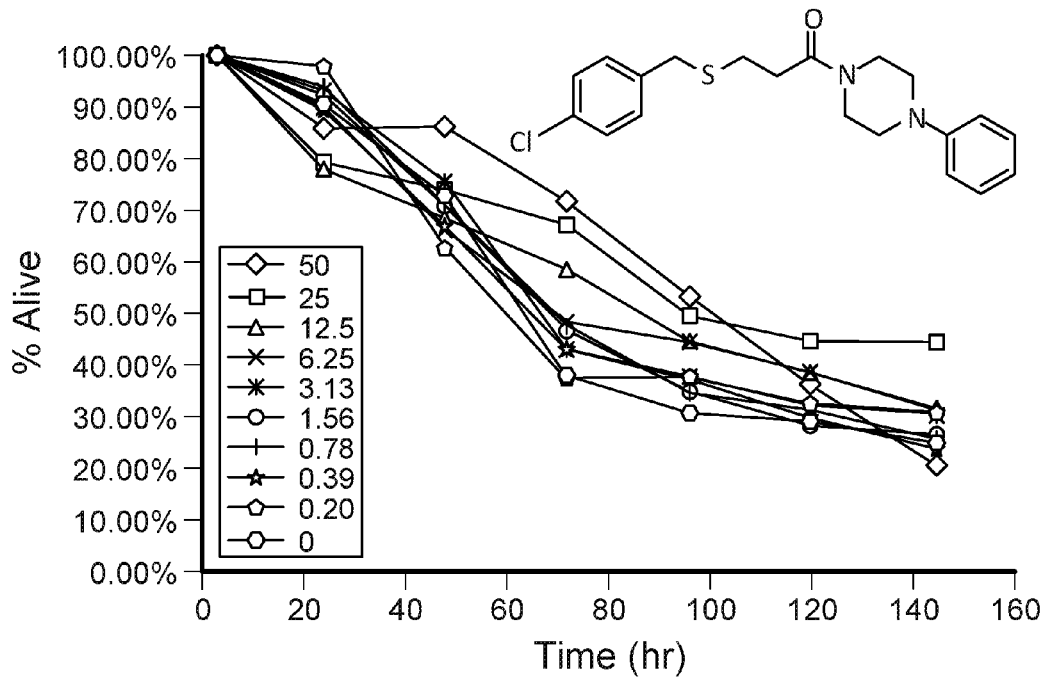
Figure 2F:
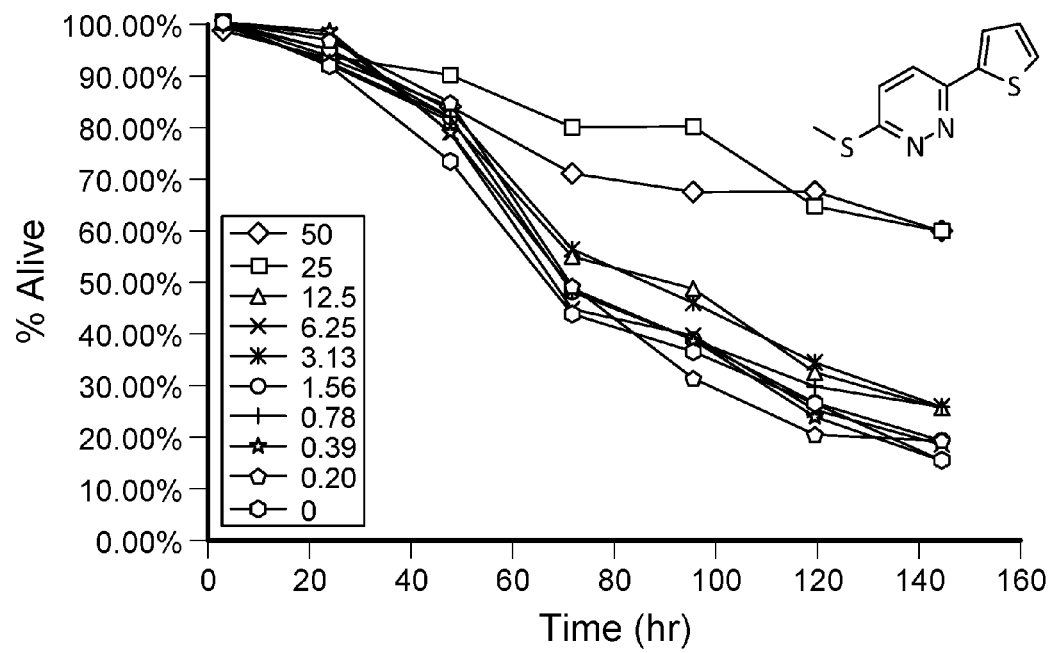

To create an automated image analysis system for high throughput screening as shown in FIG. 1A, a CELLPROFILER procedure can be created to analyze images. The major steps of this procedure are shown in FIG. 1B. In general, the area of each well that is SYTOX-positive in the fluorescence image is measured and normalized by the total area occupied by all worms, which is quantified in the bright field image. This typically requires illumination correction to flatten lighting abnormalities, adaptive thresholding, and size- and contrast-based filters and masks to exclude debris and other artifacts. By calculating the ratio of the fluorescent area (which corresponds to the area occupied by dead worms) to the total area occupied by all worms, one can accurately determine the number of dead worms in each well. For example, as shown in FIG. 1B, when 12 of the 14 worms were dead in a well as scored manually by shape (live worms are sinusoidal whereas dead worms are rigid rods), the ratio of the fluorescent area to the area occupied by all worms obtained by the CELLPROFILER analysis is 0.78. In a well where the worms are rescued by ampicillin treatment, 3 of the 14 worms were dead based on manual scoring. The ratio of the fluorescent area to the area occupied by all worms obtained by the CELLPROFILER analysis is correspondingly low at 0.12.

The CELLPROFILER analysis method can be sufficiently accurate for automated, high throughput screening. Indeed, experimental results show that the fraction of dead worms in the well treated with ampicillin can be easily separated from the fraction of dead worms in a control plate by the CELLPROFILER analysis. For example, in an assay with duplicate 384-well plates where half of the wells contain 21 µg/ml ampicillin and the other half contained DMSO as a mock treatment, there was no overlap in survival scores (which equal one minus the ratio of fluorescent area of SYTOX-stained worms to total worm area in a well) between the mock treatment (range=0 to 0.3) and the antibiotic treatment (range=0.85 to 0.95). In other words, the mean scores of the control populations are separated by several standard deviations from the mean scores of the treated populations.

In addition, experimental results show that worm survival determined by the automated CELLPROFILER analysis correlates well with the manual scoring method in a simple regression line. It is possible that there is a small fraction of worms that appear dead based on their body shape (i.e., rigid rod) but does not stain with SYTOX, and there is another small fraction of worms that appear alive based on their body shape (i.e., sinusoidal) but are SYTOX-stained. These discrepancies may be due to variability in SYTOX staining, autofluorescence that occurs in sick or dying worms, or SYTOX staining of dying cells in worms that are still alive. To make the automated analysis directly comparable to the more conventional shape-based scoring method, algorithms can be developed to identify and measure the shape of individual worms to avoid the above discrepancies.

Whole-organism (e.g., *C. elegans* or plant seedling) screening methods can also have several advantages compared to in vitro screening methods that use planktonic cells. For example, some virulence traits are induced only in the host and, therefore, the identification of compounds that are effective against these virulence traits may require detection in vivo. In addition, the whole-organism approach provides relatively unambiguous assay endpoints (e.g., survival or death of the animal or plant), allows the use of liquid handling robots for filling assay plates and for pin transfer of compounds from library stock plates to assay plates, and permits automated or semi-automated readout using plate readers or automated imaging microscopes. The whole-organism assays using, e.g., invertebrates, can also have many advantages compared to screens using mammalian models. Indeed, the study of pathogenesis in mammals is complicated by difficulty of handling, long reproductive cycles, small brood sizes, complexity of mammalian hosts, high cost, and ethical considerations.

Despite the potential value of live animals (e.g., *C. elegans*, *Drosophila* or moth larvae) or plant seedlings for gene, drug, or drug-target discovery, screening methods using whole animals, prior to the present disclosure, were generally carried out manually and, therefore, were extremely labor intensive. For example, in the laboratory, *C. elegans* assays are typically carried out by transferring nematodes from lawns of *Escherichia coli* strain OP50 (their normal laboratory food) to lawns of pathogenic bacteria or yeast grown on solid agar media. However, screening chemical libraries using an agar-based *C. elegans* killing assay is not readily compatible with the use of robots for filling assay plates and pin transfer of compounds, homogeneous distribution of chemicals in the medium, or the use of automated plate readers or automated screening microscopes to monitor host (e.g., nematode) survival. The previously available liquid assays also had their deficiencies, as these assays used volumes that were incompatible with high-throughput screens of chemical libraries. The methods for identifying candidate compounds described herein can be automated, performed in a small volume of liquid (e.g., 20-100 pl), and the scoring of the compounds is automated and quantitative.

By using the whole animal screening methods described herein, a set of 30 384-well plates typically requires only 8 hours of worm dispensing. Further, the same set of 30 plates also typically requires a full day to image and another day for image analysis. Scoring the plates using the automated SYTOX live/dead assay is about five times faster than scoring the plates manually. Thus, this versatile and robust automated whole animal screening method can screen about 9,000 compounds per week per researcher, or 4,500 compounds tested in duplicate, thereby enabling a high throughput method that is previously not feasible due to the amount of labor and time required for manual scoring. The throughput can be further increased by using multiple automated systems or using a faster server to process and analyze the images.

The screening methods described herein can also be used for quantitative analysis of a wide range of biological processes such as the response to different types of biotic (e.g. pathogens) or abiotic (e.g., exposure to heavy metals, ultraviolet radiation, or heat) stresses that affect viability. Traditional longevity studies can also be performed using the methods described herein, which would allow for the automated screening of any phenotypic read-out based on fluorescent markers (e.g., green fluorescent protein, Nile Red, MitoTracker (Invitrogen), or SYTOX green or orange nucleic acid stains). Automated screening of ectopic fluorescent and luminescent markers such as GFP and luciferase could facilitate the finding of genes that affect reproduction, cell proliferation, cell death, fat accumulation, insulin signaling, pathogen resistance, and neurotransmission. In addition, the study of chemical or genetic perturbations that affect growth rate or body size could be performed using the screening method described herein.

Other features and advantages of a high throughput screening method using a whole organism are described in, for example, WO 2008/066576, the entire contents of which are hereby incorporated by reference.

Also within the scope of this disclosure are pharmaceutical compositions containing at least one compound described above and a pharmaceutical acceptable carrier. Further, this disclosure covers a method of administering an effective amount of the compounds described herein, e.g., in a pharmaceutical composition, to a patient having a bacterial infection, e.g., as described herein. "An effective amount" or "an amount effective" refers to the amount of an active compound that is required to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typical doses can range from about 0.01 µg/kg to about 50 mg/kg (e.g., from about 0.1 µg/kg to about 25 mg/kg, from about 1 µg/kg to about 10 mg/kg, from about 10 µg/kg to about 5 mg/kg, or from about 0.1 mg/kg to about 1 mg/kg) of body weight per day.

To practice the method described in the present disclosure, a composition having one or more compounds described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in buffered saline or 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as TWEENs or SPANs or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds described above can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of formulating suitable pharmaceutical compositions are known in the art, see, e.g., the books in the series *Drugs and the Pharmaceutical Sciences: a Series of Textbooks and Monographs* (Dekker, N.Y.).

The compounds described above can be preliminarily screened for their efficacy in treating above-described infections by the whole-organism screening method described herein and then confirmed by additional animal experiments and clinic trials. Other screening methods will also be apparent to those of ordinary skill in the art.

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1

High Throughput Screening Assay Based on *E. Faecalis*

Materials and Methods

Infection Assay for Primary Compound Screening.

glp-4(bn2); sek-1 (km4) mutant worms were grown to gravid adult stage. 1,000 worms at the L1 stage were grown for 5.2 days at 15° C. on 9-cm plates of SK agar media spread with a lawn of *E. coli* strain HB101. Embryos from the gravid adults were isolated by a previously described hypochlorite method (see Tan et al., (1999) Proc. Natl. Acad. Sci. USA 96, 715-720) and hatched at 15° C. for 2 days. Approximately 4,500 of the L1 hatchlings were grown on each 9-cm plate of SK-NS agar (SK media with 62.5 U/ml nystatin and 100 µg/ml streptomycin) and with lawns of *E. coli* HB101. These worms were grown at 25° C. for 52 hours to generate sterile, young adults.

A culture of *E. faecalis* MMH594 was grown in BHI broth (BD Difco) with 80 µg/ml kanamycin at 37° C. for 6 hours and 100 µl of the culture were spread onto each 9-cm plate of BHI agar containing 80 µg/ml kanamycin. Lawns of *E. faecalis* were grown at 25° C. for 16 hours and transferred to 15° C. for 8 hours.

Sterile adult worms were resuspended in M9 buffer and washed twice with M9 in a 1:10 ratio to remove *E. coli*. 8,000 worms were pipetted onto each lawn of *E. faecalis* and incubated 15 hours at 15° C. After infection, the worms were resuspended in M9 and used as described below. 384-well plates (Corning #3712) were filled with 55 µl media (see below) using a Thermo Scientific MULTIDROP Combi reagent dispenser. 0.3 µl of a candidate compound in DSMO were pin transferred into each well using a CyBio CYBI-Well vario transfer system. The plates were agitated using an Eppendorf MIXMATE at 1,800 rpm for 15 seconds. Using the Union Biometrica Complex Object Parametric Analyzer and Sorter (COPAS) BIOSORT worm sorter according to manufacturer's protocols, 15 of the infected worms were transferred to each well in a total volume of approximately 15 µl. Total volume per well is 70 µl/well with a final composition of the media being 20% BHI, 60% M9 buffer, 80 µg/ml kanamycin, 62.5 U/ml nystatin, 1% DMSO, and 19% sheath solution (Union Biometrica Part #300-5101-000). Plates were vortexed for 5 seconds, centrifuged at 1000×g for 10 seconds, and sealed with gas permeable membranes (BREATHEASY Diversified). Plates were placed in a single layer on the top shelves in a 26.3° C. incubator at 85% relative humidity (RH) and incubated without agitation for 5 days.

After 5 days, the bacteria and liquid media in the assay plates were removed as described below. First, the bacteria were re-suspended by shaking on the MIXMATE for 15 seconds at 1,800 rpm, the sealing membrane was removed, and the worms were allowed to settle to the bottom of the wells for 3 minutes. Using the BioTek ELx405 microplate washer with the BioStack plate handling system according to manufacturer's guidelines, approximately 70% of the liquid in the wells were aspirated. Subsequently, 65 µl of a M9 buffer was dispensed into the wells at a maximum speed to resuspend the well contents. After the worms were allowed to settle for at least 3 minutes, three more cycles of aspiration, dispensing and settling were performed. Lastly, one final round of aspiration was performed leaving approximately 20 µl of liquid in the well. 70 µl of 0.9 µM SYTOX Orange (Invitrogen) in M9 was dispensed into each well with the Combi dispenser to yield a final concentration of 0.7 µM of the SYTOX Orange. The plates were sealed with gas permeable membranes and incubated at 20° C. and 80% RH for 16 hours. Using a Molecular Devices Discovery-1 microscope with a transmitted light module and a 2× low magnification objective running METAEXPRESS software, images showing the entire well were captured using a TRITC filter set or with bright field transmitted light.

The screen was performed using duplicate plates. For every experiment, one set of duplicate plates consisted entirely of a mock treatment (DMSO only). Another set of duplicate plates each contained 192 wells of ampicillin at a final concentration of 21 µg/ml as a positive control and 192 wells of the mock treatment as the negative control. The screening was performed with 17 independent infection assays where a total of 33,931 compounds and 3,283 natural product extracts were screened.

Data Storage and CELLPROFILER Analysis.

All images acquired were transferred to and stored on a dedicated Dell PowerEdge 2950 server attached directly to 15 1TB SATA hard drives. Data analysis was carried out on the Dell 2950 server with CELLPROFILER using a customized procedure (i.e., a CELLPROFILER pipeline) and the resulting processed images and associated data were loaded into a custom Oracle database developed specifically for this project.

Dose Response Time Courses.

The dose dependence of certain antimicrobial compounds identified by the assay above were studied. These compounds were purchased in a larger amount from commercial sources. For each of these compounds, an infection assay was performed essentially as described above at different concentrations except that SYTOX staining was not used. Instead, bright-field images of the wells were acquired at daily time points and scored manually for worm survival by analyzing worm body positioning. The Effective Concentrations (EC) were calculated as the concentrations at which the dose response curves of a compound (converted to Kaplan-Meier survival plots) were significantly different from the mock-treated sample with a p-value <0.05, according to the logrank statistical analysis. All compounds used in this assays were confirmed for their identity and purity by liquid chromatography/mass spectrometry.

Scoring Control Plates for Manual Vs. Automated Methods Comparison.

Synchronized young adult worms were grown on *E. coli* HB101 on SK-NS agar plates at 25° C. as described above. To generate dead worms, the worms were washed with M9 buffer and then incubated in M9 buffer at 42° C. for 2 hours. A COPAS BIOSORT was used to transfer 15 live or dead worms into a 384-well plate containing M9 buffer and 0.7 µM SYTOX Orange. The worms were then incubated for 4 hours at 22° C., fluorescence and bright field images were taken for each well, and images were scored as described.

MIC Assays.

A culture of *E. faecalis* MMH594 was grown overnight in BHI broth to stationary phase at 37° C. with aeration. The culture was diluted to an approximate density of $2 \times 10^{-4}$ CFU/ml in worm infection media (20% BHI, 80% M9 buffer). 12.5 µl of the bacterial culture dilution was inoculated into 384-well plates containing 12.5 µl of 2-fold serial dilutions of a test compound. All wells had a final DMSO concentration of 1%. Plates were incubated at 37° C. for 15 hours and scored by eye for bacterial growth.

Results 33,931 compounds and 3,283 natural product extracts from several compound libraries were screened using the methods described above. Table 1 below summarizes these libraries, which include those containing known bioactives, natural product extracts, purified natural products, and synthetic compounds.

TABLE 1

Compound libraries screened and the number of members from each library identified as having curing activity in *C. elegans* infected with *E. faecalis*.

| Compound Library | # wells screened | # hits | hit rate |
|---|---|---|---|
| Bioactives | 2,000[a] | 69 | 3.50%[a] |
| Natural product extracts | 3,283 | 4 | 0.12% |
| Analyticon purified natural products | 2,477 | 18 | 0.65% |
| Diversity-Oriented Synthesis (DOS) | 11,666 | 1 | 0.01% |
| ChemBridge kinases | 8,240 | 21 | 0.27% |

TABLE 1-continued

Compound libraries screened and the number of members from each library identified as having curing activity in *C. elegans* infected with *E. faecalis*.

| Compound Library | # wells screened | # hits | hit rate |
|---|---|---|---|
| Commercial compounds: | | | |
| ChemDiv | 11,616 | 12 | 0.10% |
| TimTec | 8,512 | 7 | 0.08% |
| MayBridge | 5,448 | 3 | 0.06% |
| ChemBridge | 704 | 1 | 0.14% |
| Total | 53,946[b] | 136 | 0.24%[c] |

[a]approximate number due to redundancies
[b]33,931 unique compounds and 3,283 extracts
[c]average hit rate For each independent batch of plates, two 384-well plates that contained only the mock treatment were used. This enabled a software program utilized by the Broad Chemical Biology Platform to generate a z-score value for each sample. Z-score represents the number of standard deviations between the ratio of dead worm area and total worm area in a candidate compound-treated well and such a ratio in a DMSO-treated mock well (see Seiler et al., (2008) Nucleic Acids Res. 36, D351-359). Each screening assay also included duplicate positive and negative control plates in which half of the wells contained ampicillin or DMSO treatment. A mock well with a zero worm survival rate should have a z-score of zero and a well with increased worm survival should have a negative z-score because it has a lower ratio of dead worm area to total worm area. The results showed that the screen average for DMSO-treated wells was −0.14 with a standard deviation (i.e., z-score) of 0.71. For ampicillin-treated wells, the average was −8.70 with a standard deviation of 0.61.

In the primary screen, a composite z-score was calculated from the two replicates for each compound. The composite z-scores were sorted in ascending order and approximately the top 1% of the compounds was selected for confirmation by manual analysis of the original images based on body shape. "False-positive" wells excluded from further analysis included cases with low fluorescence signal with straight body position, debris or compound precipitation that was quantified as total worm area, the absence of worms in the well due to inaccurate worm sorting, poor image quality due to well abnormalities, or cases where only one of the two duplicate wells showed increased survival.

To determine the false negative rate of the automated analysis method, a random set of 4,954 bright-field images for one of the library collections were manually screened. 16 wells were identified to show increased survival for both duplicate wells. Fourteen of these wells were also identified by the automated analysis method. The 2 wells that were not identified by the automated analysis were missed because the worms with sinusoidal, live body position were SYTOX-positive with corresponding z-scores of 0.3 and 0.5. A similar number of bright-field images for other compound libraries were also manually screened and no more false negatives were identified, suggesting that they occur at a very low frequency.

The primary screen identified 132 compounds and 4 extracts that increased worm survival, with an overall hit rate of approximately 0.25% (see Table 1). Among the 136 primary hits, 16 pairs of duplicate compounds were from different compound libraries, indicating that the assay is consistent between experiments. There were also 5 hit compounds among the 136 primary hits that had duplicates in other libraries that were not identified as hits. In general, these latter hits had relatively weak bacterial growth inhibitory activity. Of the primary hits, 119 compounds and extracts were available for retesting in a secondary screen. 108 of the 119 compounds and extracts (91%) were retested as positive in a second experiment. Of these 108 compounds and extracts, 62 are known antibiotics and 18 others have reported antimicrobial properties or are structural somewhat similar to known antibiotics. These 80 known or suspected antibiotics include 15 of the 16 pairs of duplicate compounds. Of the remaining 28 unique hits, 21 compounds (i.e., compounds 1-4, 6-12, 14-21, 23, and 24) were purchased from commercial sources for further testing. Additionally, 2 compounds (i.e., compounds 25 and 26) that cured infected *C. elegans* in the primary screen but did not re-test in a secondary experiment were purchased for further characterization.

The Minimum Inhibitory Concentrations (MIC) of the above-mentioned 23 commercially available compounds were determined in vitro with *E. faecalis*. Dose response time course experiments were performed to determine the kinetics of their activity in the infection assay. 10 of the 23 compounds (i.e., compounds 1-4, 6-9, 11, and 25 described in the Summary section above) were found to be able to cure *C. elegans* of an *E. faecalis* infection at a significantly lower concentration than is necessary to inhibit the growth of the pathogen in vitro (the hallmark of an anti-infective compound that targets pathogen virulence or host immunity). FIGS. 2A-2F show dose response curves illustrating the curing kinetics for compounds 2, 4, 6, and 7-9 described in the Summary section above. In addition, the MIC and EC values of compounds 1-4, 6-9, 11, and 25 are summarized in Table 2 below.

TABLE 2

MIC and EC values of compound 1-4, 6-9, 11, and 25.

| Compound Number | MIC (µg/ml) | EC (µg/ml) |
|---|---|---|
| Compound 1 | 12.5 | 0.78 |
| Compound 2 | 25 | 1.56 |
| Compound 3 | 12.5 | 3.13 |
| Compound 4 | 1.56 | 0.39 |
| Compound 6 | 6.25 | 0.39 |
| Compound 7 | >100 | 25 |
| Compound 8 | >100 | 3.13 |
| Compound 9 | >100 | 3.13 |
| Compound 11 | 6.25 | 0.20 |
| Compound 25 | >100 | 25 |

As shown in Table 2, the EC values of compounds 1-4, 6-9, 11, 25 were unexpectedly lower than their respective MIC values, suggesting that they could effectively inhibit the ability of a bacterium to kill a host organism in vivo even though they did not exhibit significant in vitro antimicrobial activity.

Example 2

Inhibition of Biofilm Formation and Disruption of Biofilm Maintenance

Methods

To test the efficacy of candidate compounds on biofilm formation, a dilute bacterial culture of *Enterococcus faecalis* was incubated with candidate compounds in polystyrene plates and the level of biofilm formation was quantified by measuring the amount of crystal violet absorbed by the biofilm mass attached to plastic. First, *E. faecalis* strain V583 was grown at 37° C. for 16 hours in Tryptic Soy Broth (TSB) with 1% glucose. The bacterial culture was diluted to $OD_{600}=0.025$ in fresh medium and was dispensed into 96-well polystyrene plates. Candidate compounds dissolved in dimethylsulfoxide (DMSO) were added to the wells to provide a final concentration of 10 µg/ml and the plates were incubated statically at 37° C. for 24 hours. After incubation, the medium was aspirated, the planktonic cells were removed by washing with phosphate buffered saline (PBS), and the plates were inverted and dried for 1 hour at room temperature. The biofilm mass was stained with 0.2% crystal violet for 15 minutes and extraneous crystal violet was washed away with PBS. The crystal violet absorbed by the biofilm was extracted with an 80% ethanol, 20% acetone mixture and the absorbance at 595 nm (OD595) was read with a spectrophotometer.

To test for the efficacy of candidate compounds on biofilm maintenance, a bacterial culture of $OD_{600}=0.025$ was grown in 96-well polystyrene plates for 24 hours as described above to establish biofilm mass prior to the addition of candidate compounds dissolved in DMSO at a final concentration of 10 µg/ml. The plates were then processed as described above.

Results

Compounds 1-4, 6, 7, and 9-11 were tested in the assays described above. Tetracycline (Tet) was used as a control. The experimental results are summarized in FIGS. 3A and 3B, in which the OD595 values represent an average of four wells and error bars represent the standard deviation.

Figure 3A:
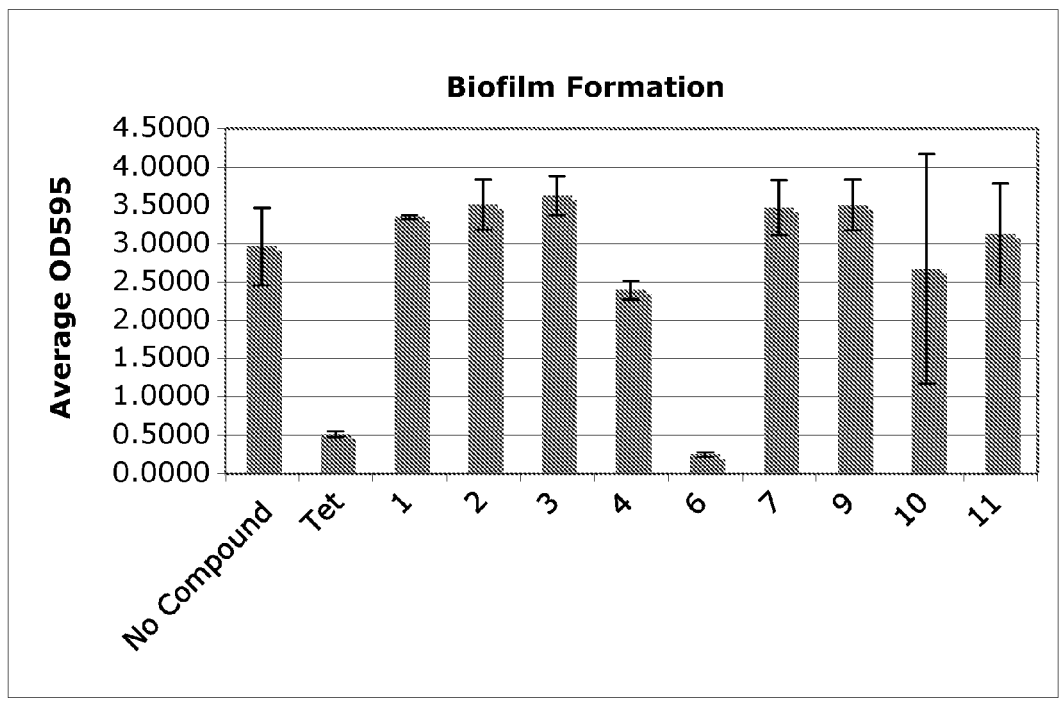
FIG. 3A is a graph illustrating the efficacy of Compounds 1-4,6,7, and 9-11 in inhibiting biofilm formation.
Figure 3B:
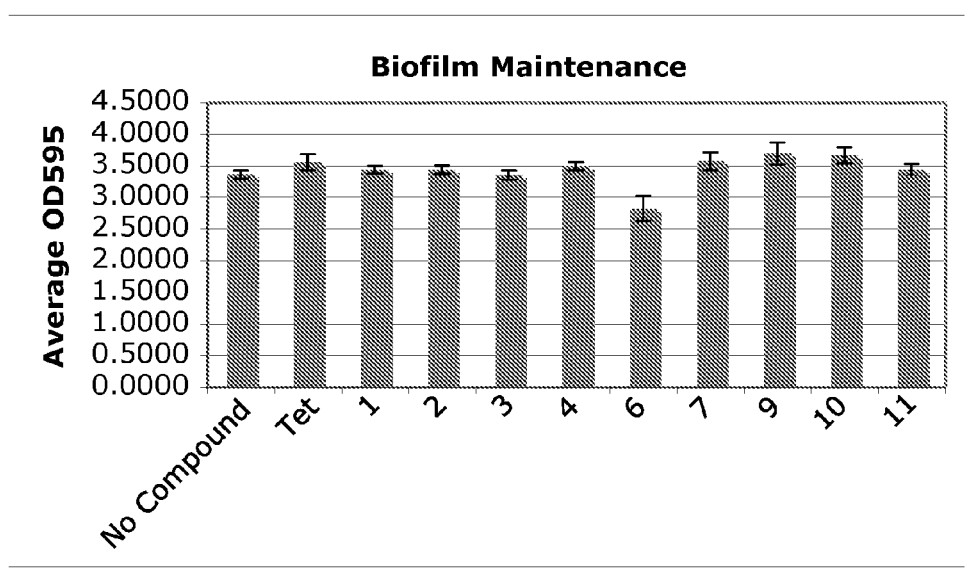
FIG. 3B is a graph illustrating the efficacy of Compounds 1-4,6,7, and 9-11 in disrupting biofilm maintenance.

As shown in FIGS. 3A and 3B, among the compounds tested, Compound 6 (a compound of formula (III)) prevented *E. faecalis* biofilm formation (see FIG. 3A) and also disrupted biofilm once it was formed (see FIG. 3B). Without wishing to be bound by theory, it is believed that Compound 6 may cause less biofilm formation by preventing the initial growth of the bacteria, as was the case with the antibiotic control tetracycline (see FIG. 3A). In addition, Compound 6 also reduced biofilm mass after a biofilm had already been established, suggesting that this compound is effective in disrupting biofilms. As shown in the results for tetracycline in FIG. 3B, the dense cell aggregate that was formed with biofilms was largely antibiotic-resistant. Thus, it is believed that Compound 6 can be more effective than tetracycline in treating *E. faecalis* infections.

Example 3

High Throughput Screening Assay Based on MRSA

Methods

To screen/test candidate compounds for their efficacy against Methicillin-resistant *Staphylococcus aureus* (MRSA) using *Caenorhabditis elegans* (*C. elegans*), a liquid high throughput screening assay was developed. In contrast to the *Enterococcus faecalis* infection assay, where worms are pre-infected with *E. faecalis* on agar prior to the start of the screening assay and then infected worms are transferred to microtiter plates using the COPAS BioSort robot, the infection of worms with MRSA occurred directly in the liquid medium. This liquid infection protocol with MRSA was developed because the COPAS BioSort, the large particle sorter used to dispense worms into multiwell plates, is a pressurized system that can generate aerosols. Because MRSA is a potentially dangerous pathogen for immune competent individuals, sorting MRSA-infected worms in the COPAS BioSort was deemed to be potentially hazardous.

In testing liquid media conditions for infecting *C. elegans* with MRSA, it was found that Brain Heart Infusion (BHI) broth, a broth commonly used to culture a variety of microorganisms and to recover difficult-to-culture organisms from infected tissues, caused many MRSA strains to produce a large quantity of exopolysaccharide (EPS) matrix. The EPS matrix manifested as sticky cell aggregates that were difficult to wash from the microtiter plates, which prevented proper SYTOX staining and scoring worm survival. On the other hand, it was found that Tryptic Soy Broth (TSB) medium was ideal for growth of MRSA strains because much less EPS was produced. In addition, it was discovered that media concentrations were an important factor for MRSA infection of *C. elegans*. When used in a 20% TSB, 80% M9 mixture, non-pathogenic *E. coli* HB101 slightly killed *C. elegans*, whereas no killing was observed by using HB101 in a 10% TSB, 90% M9 mixture.

The MRSA infection assay was carried out by incubating *C. elegans* with three MRSA strains (i.e., USA100, USA400 and MW2) in 96 or 384-well microtiter plates and assessing whether worms were live or dead after a 5 day incubation. It was found that, among the three MRSA strains tested, the MW2 strain showed the most consistent killing and resulted in the most reproducible, scorable phenotypes with the *C. elegans* infection assay.

The MRSA infection assay was performed as follows: Worms were grown on agar using non-pathogenic *E. coli* as a food source until they reached the L4/young adult stage. A small volume of M9 buffer was added to the agar plates to float worms gently off the food source. The worms were then transferred into a large conical tube and washed 2 times by allowing worms to settle, aspirating the supernatant and adding fresh M9 buffer. 15 worms were then transferred using a COPAS BioSort large particle sorter into a 96-well plate containing 35 μA of M9. MW2 culture was aliquoted into the wells to a final $OD_{600}$ of 0.01 and candidate compounds were added to the appropriate concentrations to be incubated in a final media solution comprised of 10% TSB, 90% M9 and 1% DMSO. The plates were sealed with a gas permeable membrane and incubated for 5 days, at which time the worms were washed and stained with a SYTOX Orange solution at a final concentration of 1 μM. After the worms were stained for 18 hours, images of the plates were acquired in bright field and red fluorescence channels using a Molecular Devices Discovery-1 or ImageXpress automated microscopy system. The total number of worms was counted in the bright field image and the number of dead animals are determined by positive SYTOX staining.

Results:

11 compounds (i.e., Compounds 1-4, 6-11, and 15) that were previously shown to be able to cure *C. elegans* of an *E. faecalis* infection were tested for their ability to cure an MRSA infection at low and high concentrations. Specifically, Compounds 1-4, 10, and 11 were tested at 6.25 and 12.5 μg/ml, Compounds 7, 8, and 15 were tested at 12.5 and 25 μg/ml, and Compounds 6 and 9 were tested at 25 and 50 μg/ml. Known antibiotics chloramphenicol and tetracycline were also tested as positive controls. The fraction of dead worms is an average of four wells and the error bars represent the standard deviation.

Figure 4:
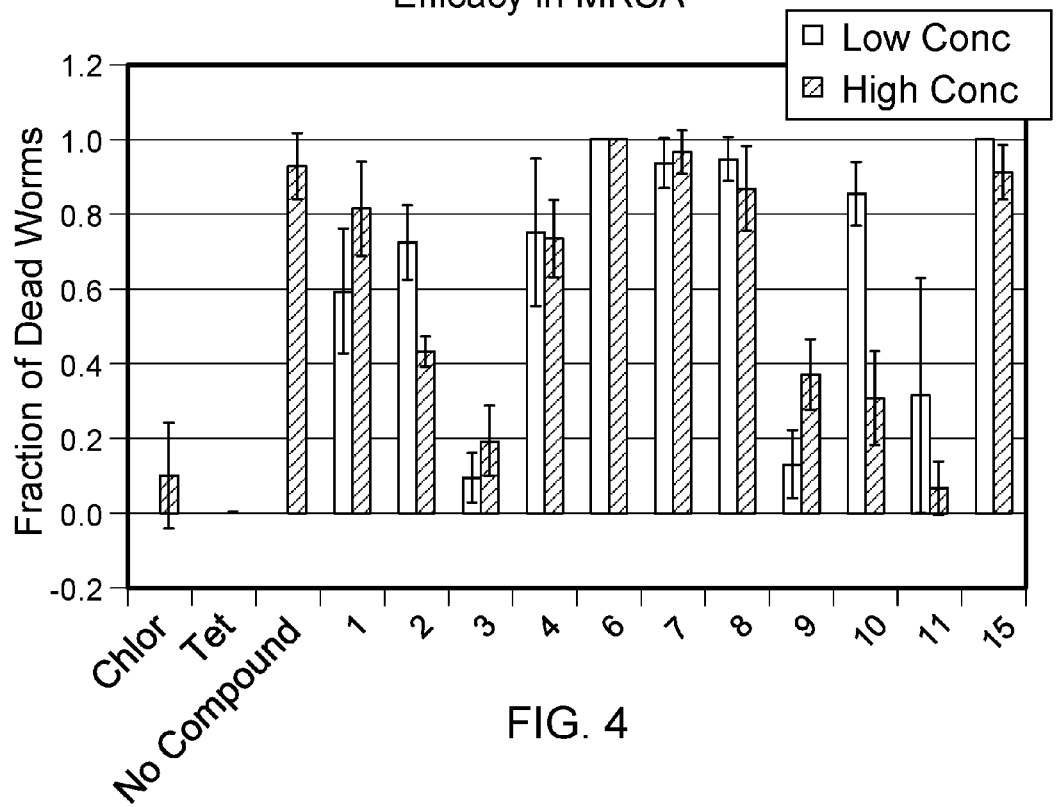
FIG. 4 is a graph illustrating the efficacy of Compounds 1-4, 6-11, and 15 in inhibiting MRSA infection in *Caenorhabditis elegans*.

FIG. 4 shows that Compounds 3 (a compound of formula (I)), 9 (a compound of formula (VI)), and 11 (a compound of formula (VII)) resulted in survival of MRSA-infected worms at both low and high concentrations (6.25 and 12.5 μg/ml for Compounds 3 and 11, and 25 and 50 μg/ml for Compound 9). Compounds 1 and 2 (compounds of formula I) were able to inhibit the *E. faecalis* infection slightly at the low concentration (6.25 μg/ml) and Compound 2 was also able to inhibit the *E. faecalis* infection better at the higher concentration (12.5 μg/ml). Compound 10 (a compound of formula (VII)) strongly promoted survival of infected worms at only the high concentration (12.5 μg/ml).

The results showed that several compounds of formulae (I) and (VII) were effective against MRSA infection. Significantly, these two classes of compounds are somewhat structurally related. The results also showed that three classes of compounds (i.e., the compounds of formulae (I), (VI) and (VII)) were able to cure *C. elegans* infected with a Gram-positive pathogen (i.e., MRSA) in addition to *E. faecalis*. These findings represent an important step toward developing novel, broad-spectrum therapeutics effective against several pathogens that are currently acquiring resistances to antibiotics used commercially.

Example 4

Immunomodulatory Activity of Novel Antimicrobials in a Whole Animal Infection Model Methods

*Caenorhabditis elegans* strains were maintained on *Escherichia coli* OP50 as described in Brenner, Genetics, 1974, 77:71-94. Wildtype N2 nematodes carrying integrated transgenes acIs219 (AU78), acIs101(AY101), agIs17 (AU133), or agIs26 (AU185) (see (1) Shivers, et al., PLoS. Genet. 2010, 6: e1000892, (2) Bolz et al., J. Biol. Chem. 2010, 285:10832-40, (3) Estes et al., Proc. Natl. Acad. Sci., 2010, 107:2153-8, and (4) Irazoqui et al., Proc. Natl. Acad. Sci., 2008, 105:17469-74) were used to assay the immunomodulatory activity of candidate compounds. For qRT-PCR experiments, RNA was extracted from synchronized young adult nematodes exposed to a candidate compound or DMSO (as a control) using TRI Reagent and reverse transcribed using the Retroscript kit (Ambion). This cDNA was then subjected to qRT-PCR analysis using SYBR green detection on a CFX1000 machine (Bio-Rad, http://www.bio-rad.com). Primers for qRT-PCR were obtained from published sequences (see Irazoqui et al., Proc. Natl. Acad. Sci., 2008, 105:17469-74 and Troemel et al., PLoS Genet. 2006, 2:e183). All values were normalized against the control gene snb-1, which does not vary under the conditions being tested. Fold change was calculated using the Pfaffl method (see Pfaffl et al., Nucleic Acids Res., 2001, 29:e45).

Results

In the original screen of 37,214 compounds and extracts for novel antimicrobials with activity against *Enterococcus faecalis* in a *C. elegans* infection assay described in Example 1, 10 compounds exhibited efficacy in curing the nematodes at concentrations significantly below the minimum inhibitory concentration required to kill the bacteria. Without wishing to be bound by theory, it was hypothesized that a subset of these compounds cured nematode infection by directly activating the innate immune response of the animal. To test this hypothesis, a multi-faceted approach was used. First, the inventors studied four *C. elegans* strains in which the promoter of the nematode immune response genes T24B8.5, F35E12.5, irg-1 and clec-60 were individually fused to GFP, generating transgenes acIs219 (AU78), acIs101(AY101), agIs17(AU133), or agIs26 (AU185), respectively, thereby allowing a visual readout of gene activity in each strain. Using these reporter strains, the ability of 33 compounds previously shown to have anti-Enterococcal killing activity in the *C. elegans* infection assay (24 of which have been described above) were tested for their ability to modulate the nematode immune response.

Figure 5:
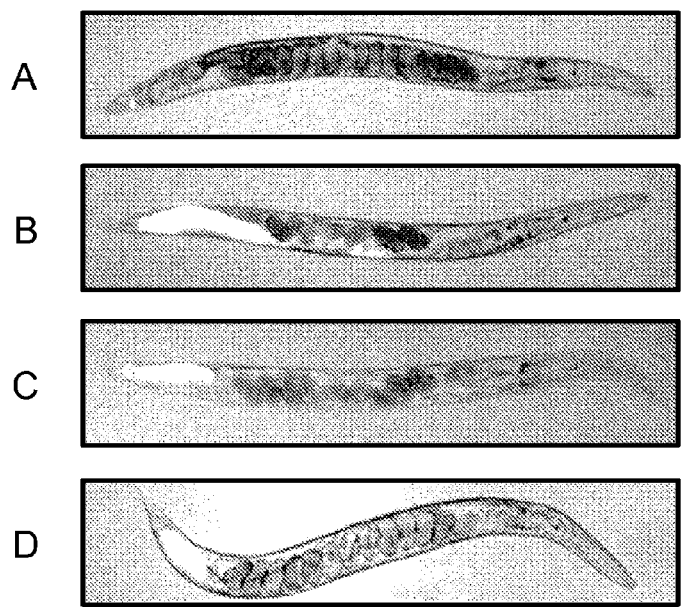
FIG. 5 illustrates *Caenorhabditis elegans* N2 worms carrying the acIs101 transgene in which the promoter for the immune response gene F35E12.5 is fused to GFP. Worms were exposed to DMSO (A), Compound 26 (B), Compound 20 (C), or Compound 25 (D).

By using the assay described above, the inventors identified five compounds (i.e., Compounds 11, 18, 20, 25, and 26) that robustly and reproducibly activated the immune GFP reporters (see FIG. 5 and Table 3) or activated selected immune response genes as determined by quantitative RT-PCR analysis (see Table 4). For the latter experiments, RNA was isolated from wild-type *C. elegans* N2 or pmk-1 mutant animals exposed to the candidate immunomodulatory compounds at 20 µg/mL and from animals exposed to DMSO. The inventors tested several immune response genes in compound-exposed animals that are known to be regulated by PMK-1, the p38 Mitogen Acitvated Protein kinase homolog, an evolutionary-conserved, central regulator of nematode immunity. The inventors also used qRT-PCR to measure the activation of several immune response genes that are known to be activated independently of PMK-1. Unexpectedly, 2 of the 5 compounds (i.e., Compounds 11 and 20) preferentially activated PMK-1-dependent immune response genes (see Table 4). Interestingly, induction of the PMK-1 dependent immune response genes by these compounds was dependent on PMK-1. Further, three compounds (i.e., Compounds 18, 25, and 26) activated at least one immune response gene in the nematode in a manner independent of PMK-1 (see Table 4). Thus, without wishing to be bound by theory, it is believed that a subset of the compounds identified in the screen for novel anti-infective compounds directly stimulate the immune response of the nematode and that these compounds act both by directly stimulating the PMK-1 pathway and by unidentified parallel immune response pathways.

TABLE 3

Immunomodulatory activity of 33 compounds with previously demonstrated anti-Enterococcal activity in the *C. elegans* infection assay was assessed by visually quantifying immune reporter induction in candidate compound-exposed versus DMSO-exposed animals.

| | | COMPOUND NUMBER | | | | |
|---|---|---|---|---|---|---|
| Transgene Array | Gene | Compound 11 | Compound 18 | Compound 20 | Compound 25 | Compound 26 |
| acIs101 | F35E12.5::GFP | + | | + | + | + |
| acIs219 | T24B8.5::GFP | + | + | | + | + |
| agIs26 | clec-60::GFP | + | | | | |
| agIs17 | irg-1::GFP | | | | | |

Five candidate compounds caused robust induction of at least one immune reporter.
+ indicates reporter induction in at least two biological replicates.

TABLE 4 qRT-PCR data comparing gene expression in animals exposed to a candidate compound versus DMSO are presented.

| | | COMPOUND NUMBER | | | | |
|---|---|---|---|---|---|---|
| GENE | GENOTYPE | Compound 11 | Compound 18 | Compound 20 | Compound 25 | Compound 26 |
| A. pmk-1 dependent immune response genes | | | | | | |
| F35E12.5 | N2 | 20.23 | 10.6 | 13.9 | 10.9 | 156.1 |
| | pmk-1(km25) | 6.7 | 0.4 | 2.9 | 8.6 | 149.0 |
| T24B8.5 | N2 | 57.0 | 2.6 | 0.4 | 1.2 | 1.6 |
| | pmk-1(km25) | 3.2 | 0.3 | 0.09 | 1.0 | 1.8 |
| C17H12.8 | N2 | 18.0 | 10.2 | 3.4 | 1.8 | 1.1 |
| | pmk-1(km25) | 1.1 | 0.3 | 0.4 | 0.3 | 0.4 |
| F56D6.2 | N2 | 15.1 | 2.2 | 10.3 | 2.6 | 13.1 |
| | pmk-1(km25) | 1.4 | 1.0 | 1.1 | 0.8 | 0.6 |
| B. pmk-1 independent immune response genes | | | | | | |
| C49G7.5 | N2 | 0.9 | 11.1 | 1.1 | 0.7 | 1.8 |
| | pmk-1(km25) | 2.5 | 57.4 | 2.9 | 0.7 | 6.3 |
| F53E10.4 | N2 | 1.0 | 0.2 | 0.2 | 0.5 | 0.3 |
| | pmk-1(km25) | 1.7 | 0.3 | 0.2 | 0.7 | 0.8 |
| irg-1 | N2 | 1.7 | 1.5 | 2.2 | 0.7 | 1.1 |
| | pmk-1(km25) | 4.7 | 4.4 | 2.1 | 1.0 | 4.0 |

Values given are the average fold-change of two biological replicates in candidate compound-exposed versus DMSO-exposed animals of the indicated genotype, following normalization with a control gene.

Example 5

In vivo Assay Based on the *C. elezans/Pseudomonas arugenosa* PA14—Infection Model Methods A liquid assay for PA14 infection of *C. elegans* in a 96-well plate format was developed. In brief, temperature-sterile glp-4 and glp-4;sek-1 worms were synchronized according to standard protocols. L1 larvae were plated, incubated for 16 hours at 15° C., and then for an additional 48 hours at 37° C., which brought them to a young adult stage. In parallel, PA14 bacteria were grown overnight prior to being plated on SK medium plates (see Tan et al., Proc. Natl. Acad. Sci., 96(2): 715-720). PA14-inoculated plates were incubated for 24 hours at 37° C. prior to an 18 hours incubation at 25° C. Subsequently, bacteria were removed from plates and resuspended in S Basal media (see Stiernagle, (2006) "Maintenance of *C. elegans*" WormBook, ed. The *C. elegans*. Research Community http://www.wormbook.org/). 96-well polystyrene plates were prepared with a medium containing either 20% SK and 80% S Basal or 50% SK and 50% S Basal, with a bacterial density of $OD_{600}$=0.03. Control wells contained 1% DMSO, and experimental wells contained 1% DMSO and Compound 11 at final concentrations 3.125, 6.25 and 20 μg/ml (growth of PA14 was previously demonstrated not to be affected by these concentrations). Dispensation of 25 young adult glp-4 or glp-4; sek-1 worms to each well using a COPAS BioSort robot brought the final total volume to 140 mL/well. After worms were added, each plate was sealed with a gas permeable membrane and incubated for 48 hours at 25° C. Plates were then washed eight times before staining with a SYTOX Orange solution at a final concentration of 2.8 μM. Worms were stained for 18 hours at 20° C. and each well was photographed using bright-field and red fluorescence channels with a Molecular Devices Discovery-1 Microscope.

Results

Figure 6:
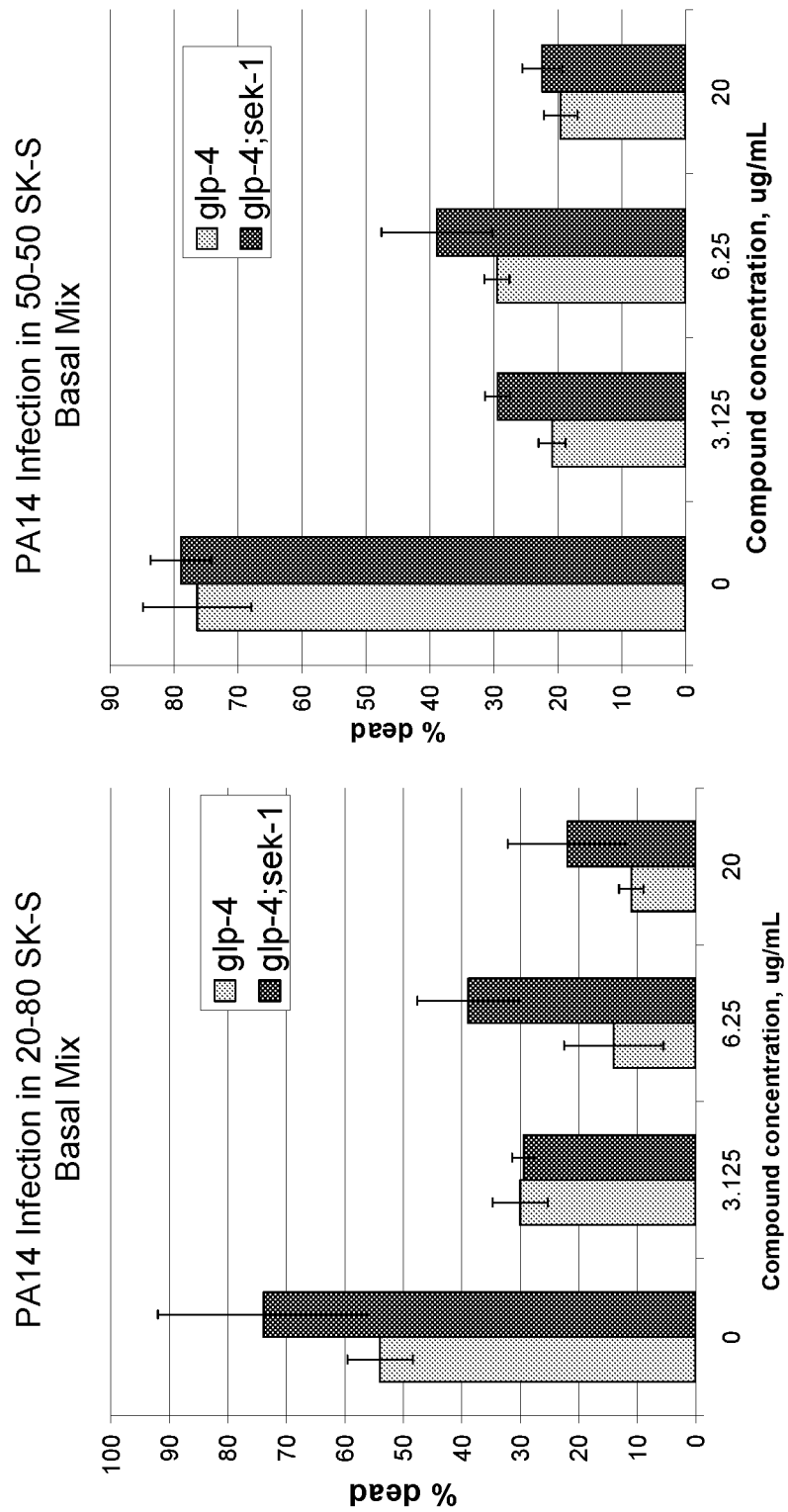
FIG. 6 illustrates the efficacy of Compound 11 in inhibiting a *P. aeruginosa* strain PA14 infection in *Caenorhabditis elegans* in two different media.

Infection of *Caenorhabditis elegans* with *Pseudomonas aeruginosa* strain PA14 resulted in a lethal pathology, as shown by control wells of infected worms (FIGS. 6A and 6B). PA14-infected, untreated glp-4 and glp-4; sek-1 worms showed 50-70% lethality in 20% SK, 80% S Basal media and roughly 75-80% lethality in a 50-50% mix of the two media types. Compound 11, which was previously identified in a high-throughput screening assay, was tested at three different dosages (i.e., 3.125, 6.25, and 20 μg/mL) for its efficacy in inhibiting PA14-infection associated lethality. Even at the lowest dosage (3.125 μg/mL), Compound 11 was capable of reducing mortality to 30% or less, half of what was observed in untreated controls. As mentioned previously, PA14 has previously been demonstrated to be unaffected by this concentration of Compound 11 (data not shown). Thus, without wishing to be bound by theory, it is believed that this compound exhibits its efficacy not by killing bacteria, but by stimulating some effect on the host in this host-pathogen interaction. In addition, without wishing to be bound by theory, it is believed that the fact that increasing the dosage of this compound did not increase its efficacy suggests that whatever stimulatory mechanism is being triggered has been saturated at the dosage of 3.125 μg/mL.

Example 6

Antimicrobial Assay

Methods

Compounds 6, 7, 15 were purchased from TimTec and ChemDiv, dissolved in DMSO at a concentration of 5 or 10 mg/ml, and further diluted in DMSO as indicated. *E. faecalis* strain MMH594 was grown overnight with aeration at 37° C. in Bacto brain heart infusion (BHI) broth (Becton Dickinson), transferred to ice, and washed in phosphate-buffered saline (PBS; pH 7.2). Equal volumes of a dissolved compound and bacteria were mixed, incubated at room temperature for 1 to 30 minutes, ten-fold serially diluted in PBS, and plated in 10 μA droplets on BHI agar plates. Plates were incubated at room temperature until colonies were visible.

Results

Figure 7A:
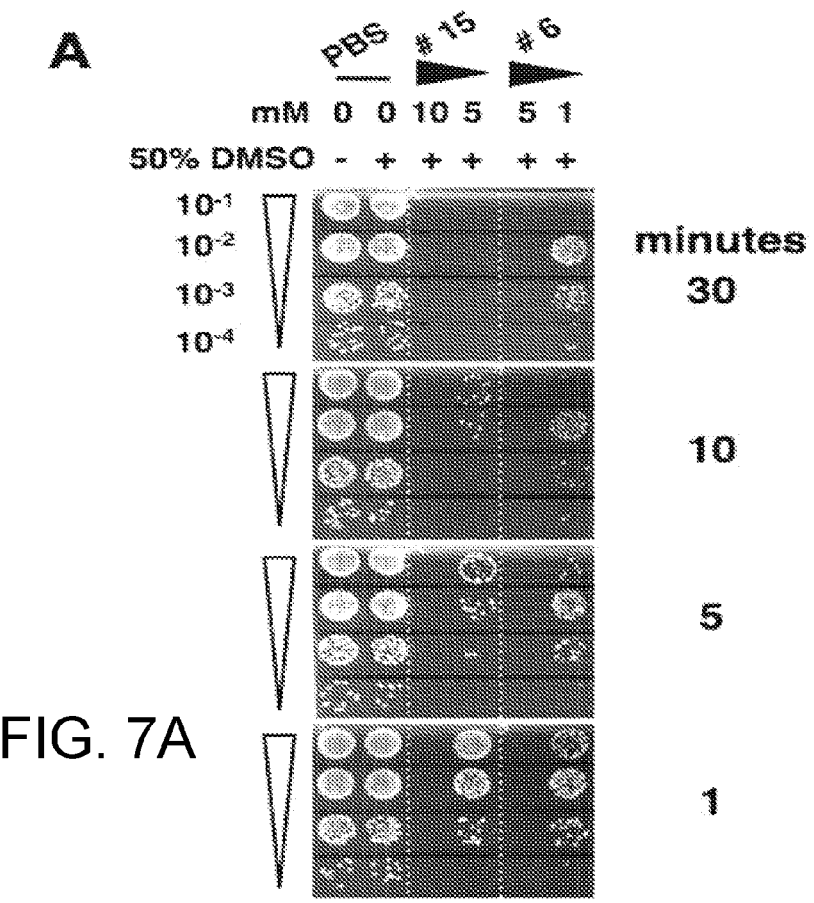
FIG. 7A is a graph illustrating the efficacy of Compounds 6 and 15 in killing *E. faecalis* strain MMH594 at the indicated concentrations for the indicated times.
Figure 7B:
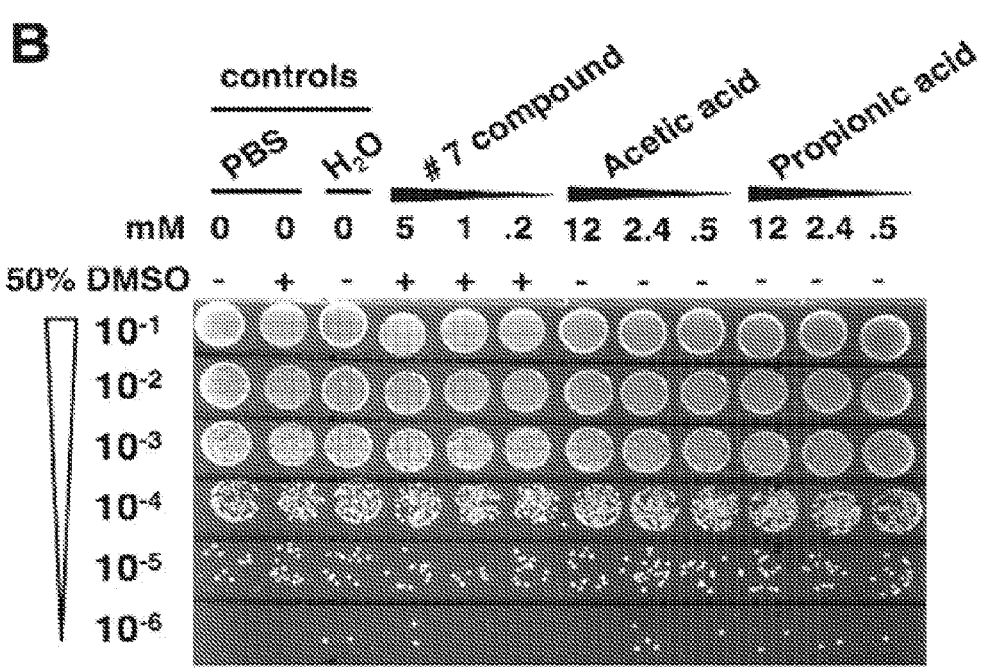
FIG. 7B is a graph illustrating that Compound 7, acetic acid, and propionic acid did not show any significant effects in killing *E. faecalis* strain MMH594.

As shown in FIGS. 7A and 7B, Compounds 6 (a compound of formula (III)) and 15 showed rapid killing of bacteria at the level of mM concentrations. Bacterial killing was time- and concentration-dependent (see FIG. 7A). Pre-incubation of bacteria with a solvent (i.e., DMSO) showed no bactericidal effect when compared to PBS (see FIG. 7A) or water (see FIG. 7B). Likewise, Compound 7 (a compound of formula (IV)), acetic acid, and propionic acid did not show any bactericidal activity (see FIG. 7B). Compounds 6 and 15 are both carboxylic acids that are weaker than acetic acid and propionic acid. In other words, the results showed that stronger carboxylic acids showed no bactericidal activity under similar conditions. In addition, neutralization with equimolar amounts of sodium hydroxide did not alter the bactericidal activity (data not shown). Furthermore, out of 23 compounds (i.e., Compounds 1-4, 6-12, 14-21, and 23-26) that possess in vivo antibacterial activity in *C. elegans*, only Compounds 6 and 15 showed bactericidal activity when tested in a *Drosophila* infection-survival bioassay (data not shown).

In sum, experiments suggest that Compounds 6 and 15 have a unique and novel anti-bacterial activity. This anti-bacterial activity was not restricted to *E. faecalis* strain MMH594, since a different *Enterococcus faecalis* strain, and a *Staphylococcus aureus* strain were also killed by these compounds (data not shown).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical composition, comprising a pharmaceutically acceptable carrier and

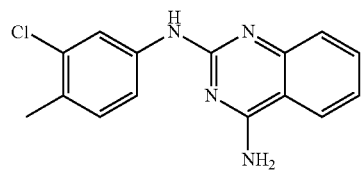

2. A method of treating a bacterial infection in a subject in need thereof, comprising administering to the subject the pharmaceutical composition of claim 1 in an amount effective to treat the infection;
   wherein the bacterial infection is gastro-intestinal tract infection.

\* \* \* \* \*